US009012869B2

(12) United States Patent
Andersson-Engels et al.

(10) Patent No.: US 9,012,869 B2
(45) Date of Patent: Apr. 21, 2015

(54) SYSTEM, METHOD, AND LUMINESCENT MARKER FOR IMPROVED DIFFUSE LUMINESCENT IMAGING OR TOMOGRAPHY IN SCATTERING MEDIA

(75) Inventors: Stefan Andersson-Engels, Lund (SE); Can Xu, Lund (SE); Haichun Liu, Lund (SE); Johan Axelsson, Lund (SE); Niclas Svensson, Lund (SE); Pontus Svenmarker, Lund (SE)

(73) Assignee: Lumito AB, Lund (SE)

( * ) Notice: Subject to any disclaimer, the term of this patent is extended or adjusted under 35 U.S.C. 154(b) by 778 days.

(21) Appl. No.: 13/318,403

(22) PCT Filed: May 5, 2010

(86) PCT No.: PCT/EP2010/056127

§ 371 (c)(1), (2), (4) Date: Jan. 12, 2012

(87) PCT Pub. No.: WO2010/128090

PCT Pub. Date: Nov. 11, 2010

(65) Prior Publication Data

US 2012/0104281 A1 May 3, 2012

Related U.S. Application Data

(60) Provisional application No. 61/215,881, filed on May 12, 2009, provisional application No. 61/255,139, filed on Oct. 27, 2009.

(30) Foreign Application Priority Data

May 5, 2009 (SE) ....................................... 0950313

(51) Int. Cl.

| | |
|---|---|
| ***G01N 21/64*** | (2006.01) |
| ***A61B 5/00*** | (2006.01) |
| ***G01N 21/47*** | (2006.01) |

(52) U.S. Cl.

CPC ............. *A61B 5/0059* (2013.01); *A61B 5/0068* (2013.01); *A61B 5/0073* (2013.01); *G01N 21/4795* (2013.01); *G01N 21/6428* (2013.01); *G01N 21/6456* (2013.01)

(58) Field of Classification Search

CPC ...................................................... G01N 21/64
USPC ...................................................... 250/459.1
See application file for complete search history.

(56) References Cited

U.S. PATENT DOCUMENTS 5,451,785 A 9/1995 Faris (Continued)

FOREIGN PATENT DOCUMENTS

JP 2004-514133 5/2004

(Continued)

OTHER PUBLICATIONS

Yi et al.; "Water-Soluble $NayF_4$:Yb,Er (Tm)/$NaY_4$/Polymer Core/Shell/Shell Nanoparticles with Significant Enhancement of Upconversion Fluorescence;" Chem. Mater., vol. 19, pp. 341-343, 2007.

Lu et al.; "Synthesis and Characterization of Multi-Functional Nanoparticles Possessing Magnetic, Up-Conversion Fluorescence and Bio-Affinity Properties;" J. Mater.Chem., vol. 14, pp. 1336-1341, 2004.

(Continued)

*Primary Examiner* — David Porta
*Assistant Examiner* — Faye Boosalis
(74) *Attorney, Agent, or Firm* — Knobbe, Martens, Olson & Bear, LLP

(57) ABSTRACT

A method and system for luminescence molecular imaging or tomography of a region of interest in a scattering medium is disclosed. The system comprises a non-linear luminescent marker material arranged in the scattering medium. Contrast and resolution of the imaging or tomography is thus improved. The non-linear marker is for instance configured to upconvert incoming light of an illumination wavelength. The non-linear power dependence of the marker enables further improvement of the imaging by using images taken with two or more excitation beams simultaneously.

37 Claims, 15 Drawing Sheets

(a) 504 504 503 502 5 mm 501 500 (c) 504 17 mm D 503 508 30 mm 503 501 505 30 mm 506 507 b) 509 508

(56) References Cited

U.S. PATENT DOCUMENTS

| | | | | |
|---|---|---|---|---|
| 8,389,958 | B2 * | 3/2013 | Vo-Dinh et al. | 250/459.1 |
| 2004/0162491 | A1 | 8/2004 | Pfister et al. | |
| 2007/0249943 | A1 | 10/2007 | Texier-Nogues et al. | |

FOREIGN PATENT DOCUMENTS

| | | | |
|---|---|---|---|
| JP | 2004-177408 | | 6/2004 |
| JP | 2006-023382 | A | 1/2006 |
| JP | 2006-026017 | A | 2/2006 |
| JP | 2006-511473 | | 4/2006 |
| JP | 2007-528500 | | 10/2007 |
| JP | 2008-149154 | A | 7/2008 |
| WO | WO 02/40974 | A2 | 5/2002 |
| WO | WO 2004/026344 | A1 | 4/2004 |
| WO | WO 2005/089637 | A2 | 9/2005 |
| WO | WO 2007/078262 | | 7/2007 |
| WO | WO 2008/048190 | | 4/2008 |
| WO | WO 2009/046392 | | 4/2009 |

OTHER PUBLICATIONS

Yi et al.; "Synthesis, Characterization, and Biological Application of Size-Controlled Nanocrystalline $NaYf_4$:Yb, Er Infrared-to-Visible Up-Conversion Phosphors;" Nano Letters, vol. 4, No. 11, pp. 2191-2196, 2004.

Xu, et al., "Autofluorescence Insensitive Imaging Using Upconverting Nanocrystals in Scattering Media," Applied Physics Letters, AIP, American Institute of Physics, vol. 93, No. 17, Oct. 27, 2008.

Rativa et al., "Silver Nanoparticles in Nonlinear Microscopy," Microwave and Optoelectronics Conference, 2007, IMOC 2007, SBMO/IEEE M TT-S International, IEEE, PI, pp. 478-482, Oct. 29, 2007.

Cambaliza et al., "Advantages of Two-Color Excitation Fluorescence Microscopy With Two Confocal Excitation Beams," Optics Communications, vol. 184, No. 1-4, pp. 25-35, Oct. 1, 2000.

International Search Report and Written Opinion in PCT/EP2010/056127 dated Jul. 22, 2010.

* cited by examiner

SYSTEM, METHOD, AND LUMINESCENT MARKER FOR IMPROVED DIFFUSE LUMINESCENT IMAGING OR TOMOGRAPHY IN SCATTERING MEDIA

This application is the U.S. National Phase under 35 U.S.C. §371 of International Application PCT/EP2010/056127, filed May 5, 2010, designating the U.S., and published in English as WO 2010/128090 on Nov. 11, 2010, which claims priority to Swedish Patent Application No. 0950313.7, filed May 5, 2009, to U.S. Provisional Application No. 61/215,881, filed May 12, 2009 and to U.S. Provisional Application No. 61/255,139, filed Oct. 27, 2009 the entire contents of which are incorporated herein by reference.

FIELD OF THE INVENTION

This invention pertains in general to the field of photoluminescence imaging or photoluminescence tomography of absorbing and scattering media, as well as photoluminescent markers for such photoluminescence imaging of scattering media or for such photoluminescence tomography of scattering media.

BACKGROUND OF THE INVENTION

An example of a scattering medium which is of interest for photoluminescence imaging (in short luminescence imaging) or photoluminescence tomography (in short luminescence tomography) is biological tissue. Tissue optics is a field devoted to study the interaction of light with such tissue. Over the last decades, the field has grown rapidly. With increasing knowledge of the light-tissue interaction, the interest in applying tissue optics as a diagnostic tool is also emerging, reaping the fruits from the fundamental research.

An area in tissue optics, which the present disclosure is partly dealing with, is photoluminescence imaging including photoluminescence tomography, which are non-invasive approaches for in-vivo imaging of humans or animals. These imaging approaches are luminescence-based and require an external source of light for excitation of luminescent biological markers.

Photoluminescence is a process in which a substance absorbs photons and then re-radiates photons. A specific form of luminescence is fluorescence, where typically emitted photons are of lower energy than those used for illumination. Thus, in fluorescence, the fluorescent wavelength is Stokes shifted to a longer wavelength with reference to the wavelength of the illuminating light.

Fluorescent imaging is known and can, for example, be used to study biological responses from drugs in small animals over a period of time, without the need to sacrifice them.

Shimomura, Chalfie and Tsien were rewarded with the Nobel prize in 2008 for discovering and developing the green fluorescent protein, which has become a very important fluorescent marker.

However, hitherto, fluorescence molecular imaging and tomography systems for diffuse luminescent imaging or diffuse luminescent tomography in absorbing and scattering media suffer from a number of drawbacks. They have for instance a low resolution or contrast, which makes diagnostic tasks based on the imaging results difficult. Hence, there is a need for such systems having improved image quality, e.g. by improved contrast and/or resolution of the two-dimensional or three-dimensional images provided.

Further, these systems are sensitive to ever-present endogenous tissue autofluorescence, deteriorating measurement results. Since the fluorescence signal from the fluorescent biological markers and the background autofluorescence often overlaps, separating them is difficult and often not reliably possible.

The autofluorescence conceals the fluorescence signal when using Stokes-shifted fluorophores, effectively limiting the signal-to-background sensitivity.

Thus, there is a need for an improved diffuse luminescent imaging or luminescent tomography system, method or luminescent markers for luminescent imaging or luminescent tomography which in particular allow for increased effectiveness by improved contrast and/or improved imaging resolution.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system, a method, and uses according to the appended patent claims.

In this present disclosure, it is shown that by replacing the traditional Stokes-shifted fluorophores with a new type of luminescent markers, namely non-linear markers, the above objects and improvements are achieved.

According to a first aspect of the invention, a method of imaging a region in a scattering medium by diffuse luminescence molecular imaging is provided. The region comprises at least one luminescent marker arranged in the scattering medium at a marker position, where the luminescent marker is a non-linear luminescent marker. The method comprises exciting the luminescent marker by excitation light emitted by one or more light sources into an excitation volume from at least one light source position, detecting luminescence from the luminescent marker due to the excitation light by a detector at a luminescent light detection position, providing movement between the light source position and the marker position, and imaging the luminescent marker based on a non-linear dependence of the detected luminescence on the excitation light intensity and the light source position in relation to the marker position.

According to a second aspect of the invention, a system for diffuse luminescence molecular imaging of a region of interest in a scattering medium is provided. The system comprises a luminescent marker for use in the luminescent molecular imaging of the scattering medium, where the luminescent marker is a non-linear luminescent marker arranged in the scattering medium. The system comprises one or more light sources positioned by at least one light source position for exciting the luminescent marker by excitation light emitted by the one or more light sources into an excitation volume. The system comprises a detector at a luminescent light detection position detecting luminescence from the luminescent marker due to the excitation light, wherein the luminescent molecular imaging comprises imaging the luminescent marker based on a non-linear dependence of the detected luminescence on the excitation light intensity and the light source position in relation to the marker position.

In embodiments the luminescent marker is comprised in a group of non-linear luminescent markers configured to upconvert incoming light of an illumination wavelength, such that luminescence occurs at a luminescence wavelength that is shorter than said illumination wavelength when said luminescent marker is illuminated with said incoming light.

The luminescent marker is in certain embodiments a biological luminescent marker.

According to another aspect of the invention, a use of a system of the second aspect of the invention is provided for luminescence imaging or tomography of tablets.

According to another aspect of the invention, a use of a system of the second aspect of the invention is provided for in-vivo or in-vitro luminescence imaging or tomography of a small animal.

According to another aspect of the invention, a use of a system of the second aspect of the invention is provided for functional diagnostics, such as cancer diagnostics, by said luminescence imaging or tomography.

In an embodiment, the non-linear markers are attached to an imaging contrast agent for another imaging modality. For instance a non-linear marker is attached to a contrast agent for imaging with a conventional imaging modality, such as Magnetic Resonance Imaging (MRI), X-Ray, etc. In a specific embodiment, a non-linear marker is attached to an organic gadolinium complex or gadolinium compound, which has paramagnetic properties.

Further embodiments of the invention are defined in the dependent claims, wherein features for the second and subsequent aspects of the invention are as for the first aspect mutatis mutandis.

Some embodiments provide for increased resolution in diffuse luminescence molecular imaging and in fluorescence molecular tomography.

Some embodiments provide for determination of distribution of ingredients in tablets. For instance, a non-linear luminescent marker or fluorophore may be attached to an active ingredient in a tablet. The spatial distribution of the active ingredient may thus advantageously be determined.

Some embodiments provide for enhanced contrast in medical magnetic resonance imaging, when non-linear markers are used as an MRI contrast agent. At the same time, luminescence imaging or tomography may be made, providing for functional diagnostic information combined with high resolution MRI of one and the same region of interest and in-vivo.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
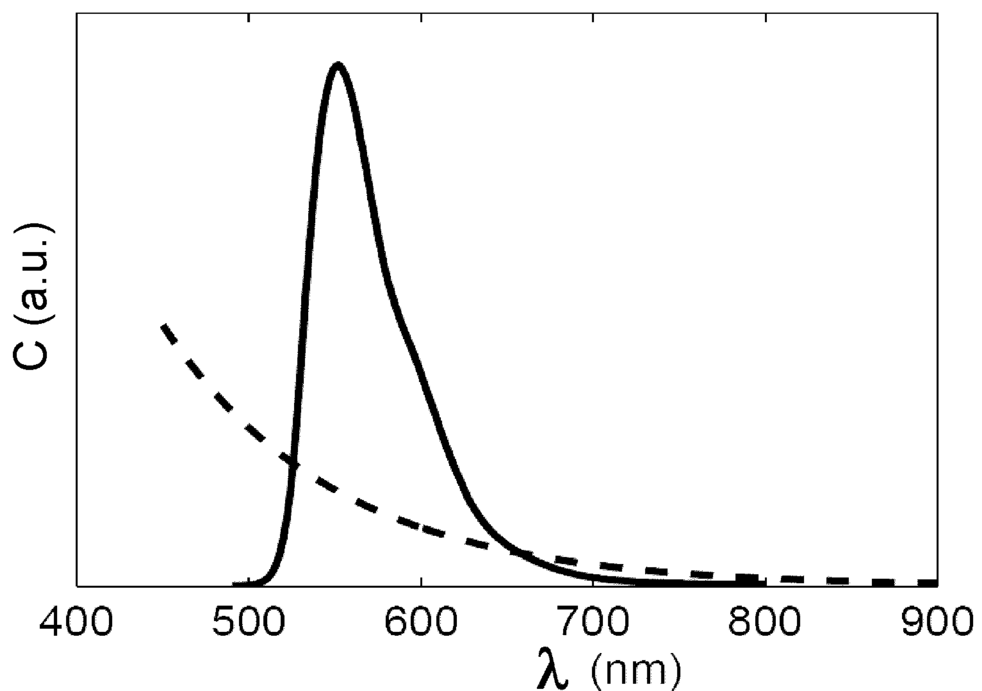
FIG. 1 is a graph showing a typical signal with an autofluorescence background.

Some embodiments of this disclosure pertain to an area within the aforementioned tissue optics dealing with diffuse luminescence imaging and tomography. For most visible wavelengths, light does not penetrate more than a few millimeters into tissue. But in the diagnostic window (wavelength 600 to 1600 nm), the light penetration is sufficient to allow imaging through up to several centimeters. This opens up the possibility of imaging fluorescent contrast agents deep in tissue. Fluorescent imaging of diffusely scattered light has a notable importance in biomedical applications.

Fluorescence tomography is based on three-dimensional reconstructions of contrast agent distributions inside humans or animal. The three-dimensional reconstructions are based on fluorescence imaging techniques.

As mentioned above, the area of fluorescence imaging and tomography of diffusely scattered light has long been adversely affected by the ever-present endogenous tissue autofluorescence, and suffered from poor contrast and resolution. The autofluorescence conceals the signal from the contrast agents when using Stokes-shifted fluorophores, effectively limiting the signal-to-back-ground sensitivity.

Experiments on tissue phantoms, with realistic optical properties, were performed, and it was shown that it is possible to detect an auto-fluorescence-free signal. Also, using the nanocrystals for three-dimensional tomographic reconstruction is disclosed.

Hence, non-linear markers, such as upconverting nanocrystals, are shown being important biological markers for tissue imaging purposes.

Several applications within biomedical imaging of the fluorescence imaging or tomography are described below. This is a specific case for scattering media. Other applications are provided in non-biological areas. Examples for such areas are luminescent imaging or tomography for material testing, including quality control of tablets, filters for liquids or gases through which flows a medium with non-linear markers, etc.

In the context of the present application and embodiment of the invention, fluorescence imaging represents all types of imaging of luminescence. Also, any imaging or tomography discussed is in highly scattering media, traditionally providing poor resolution due to the diffuse character of the light detected. Embodiments of the present invention advantageously improve contrast and resolution of such luminescent imaging, including in luminescent tomography.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Below, an overview of the fundamentals of fluorescence imaging and tissue optics are given, followed by a description of non-linear markers, such as upconverting nanocrystals, and fluorescence optical tomography using upconverting nanocrystals. Moreover, results from experiments and simulations are disclosed. In the text below fluorescence imaging represents all types of imaging of luminescence. Also, any imaging or tomography discussed is in highly scattering media, providing poor resolution due to the diffuse character of the light detected.

Fluorescence Contrast

Figure 1A:
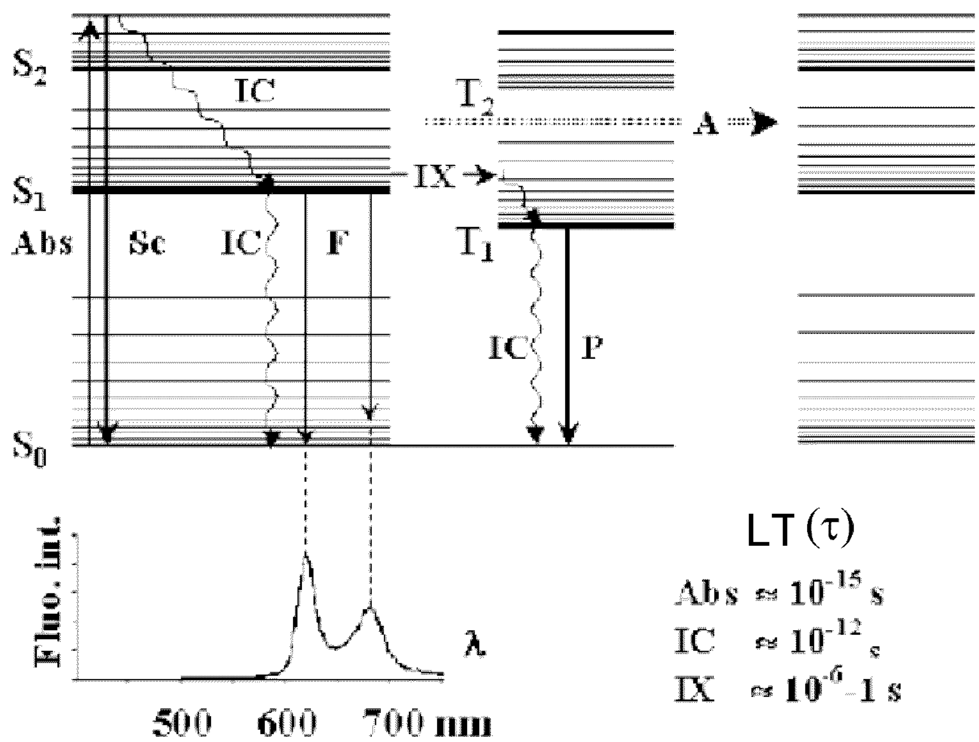
FIG. 1A is a Jablonski diagram.

The process of light emission from a fluorescing molecule (fluorophore) can be described in a Jablonski diagram, see FIG. 1A. FIG. 1A shows a Jablonski diagram showing the various decay paths from an excited state of a molecule. In the lower part of the figure, a fluorescence spectrum from haematoporphyrin in ethanol is shown. The abbreviations are: Sn: singlet states; Tn: triplet states; Abs: absorption; Sc: scattering; IC: internal conversion; F: fluorescence; IX: intersystem crossing; P: phosphorescence; A: transfer to other molecules. Also the approximate time-scale for some processes is shown down right in FIG. 1A, as lifetimes (LT), also denoted $\tau$.

If an incoming photon has an energy that corresponds to the gap between two energy bands in the molecule, it can be absorbed. The photon energy will thereby be used for excitation of the molecule to the higher energy band. Excited states are unstable and the molecule will return to the ground state. The deexcitation may follow a number of different pathways, as illustrated in FIG. 1A. The labelled levels are electronic levels, corresponding to the energy levels of atoms. S0, S1, etc. are singlet states for which the sum of the electron spin quantum numbers is zero, while T0, T1, etc. are triplet states for which the spin of one electron has changed sign. For large molecules the intervals between the levels are very small and the states overlap due to molecular interactions. When a photon is absorbed by a molecule it will not necessarily excite the molecule to the lowest vibrational level in the excited electronic level, but more likely to a higher vibrational state. This is a result of the Franck-Condon principle stating that during the rapid ($10^{-15}$ s) absorption process, the atoms do not change their location in the vibrational motion. When a molecule is excited to a high energy level, a rapid relaxation to the lowest rotational-vibrational state of S1 will follow. The short time scale ($10^{-12}$ s) of this relaxation is due to the high density of rotational vibrational levels. From S1 the molecules can proceed to the state S0 through radiationless kinetic interactions. This is called internal conversion (IC).

Alternatively, the de-excitation may result in the emission of a photon and this process is called fluorescence. Since the transition may be terminated in any of the rotational-vibrational states of S0, the energy of the different photons will not have a distinct value, but rather a broad distribution. Thus, a fluorescence spectrum from a molecule will be broad, most often without any significant structures. The form of the spectrum will reflect the probability of transitions to the lower levels (S0). In the lower part of FIG. 1A the fluorescence spectrum of haematoporphyrin, which is a tumour marker, or photosensitizer, and will be discussed later on, is shown. Once the pathway absorption-IC-fluorescence is completed, the molecule is back in its original state and configuration. Hence, the fluorescence process is non-destructive and reversible, which is an advantage in, for instance, medical diagnostics.

Although spin forbidden, a transition to the triplet system may occur. Also in the triplet system a rapid internal conversion to the lowest excited state will occur. Since a transition to S0 is spin forbidden, this will proceed at a much lower rate (t $10^{-6}$-1 s) than the transition S1 S0. This process is called phosphorescence and is less often observed at room temperature.

Several other paths are possible for the excited molecule, such as energy transfer to other molecules, electron transfer, excimer formation and excitation to repulsive states leading to molecular dissociation. These processes are indicated with an A in FIG. 1A.

Many fluorescent molecules have one important feature in common, that is the unbroken chain of conjugated double bonds, i.e. every second bond is a double bond. The structure of haematoporphyrin is an example for this (not shown). This is a fluorescent molecule used for fluorescence diagnostics and photodynamic therapy of tumours.

With the knowledge of the fluorescence properties of important tissue fluorophores, a fluorescence recording of an unknown sample will yield the relative contribution of each fluorophore. If the fluorescence characteristics are the same as for the isolated fluorophores, the concentration of the fluorophores can be estimated. This is, however, not always the case. Rather, the fluorescence properties are dependent on environmental factors such as polarity and pH.

Another important aspect of fluorescence is the rapid relaxation in the excited as well as in the ground state. The molecule looses some of its excitation energy by relaxation. Also, redistribution of solvent dipoles around the fluorophore and specific interactions, such as hydrogen bonding, contribute to this relaxation procedure. Thus, the energy of the fluorescence photons is lower than that of the excitation, or in other words, the fluorescence wavelength is longer than the excitation wavelength. This is called Stokes shift and is different for different molecular environments. Hence, a general knowledge of the molecular environment is required for an adequate fluorescence diagnosis.

Fluorescence Imaging

Figure 5:
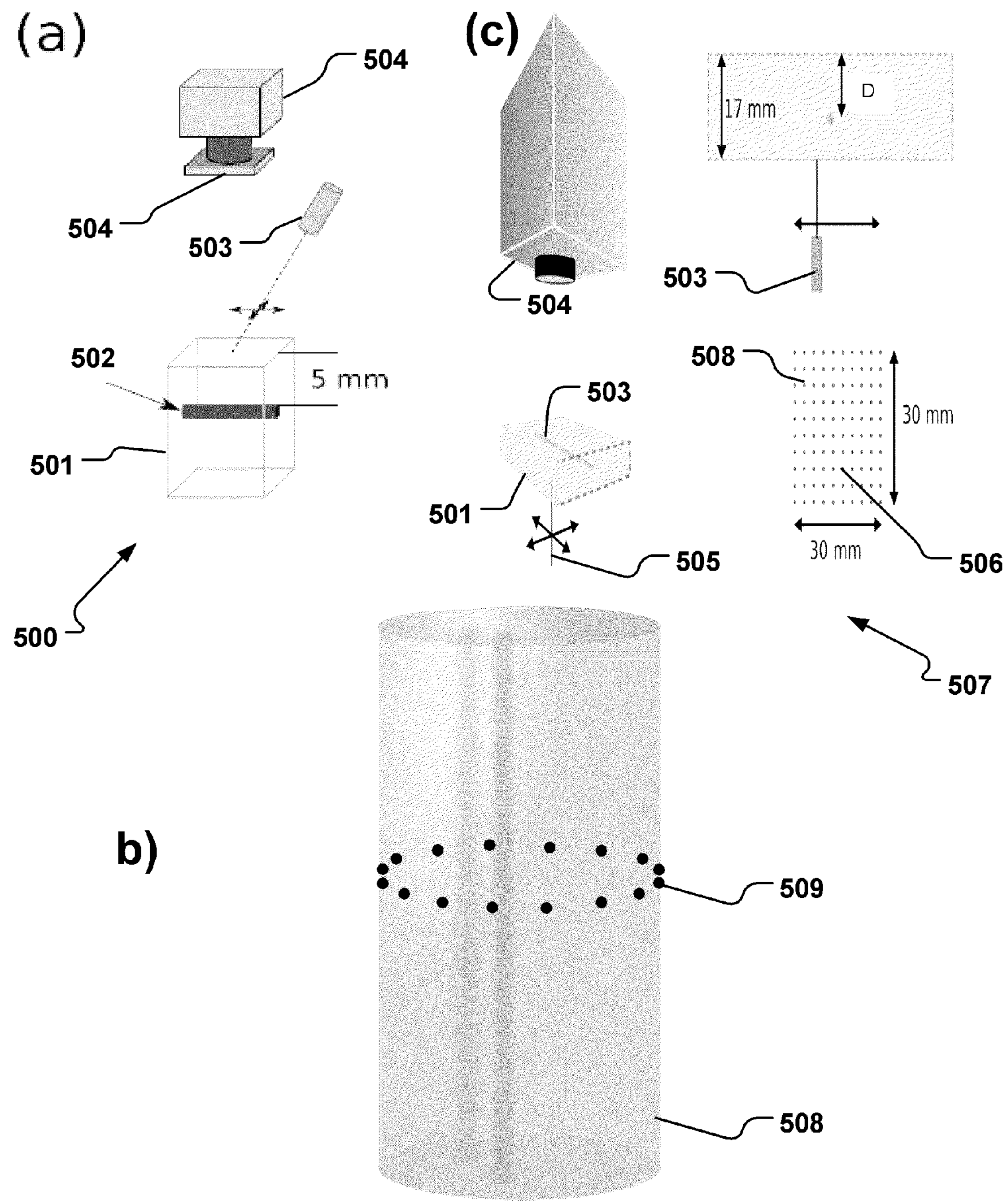
FIGS. 5a), b) and c) are schematic illustrations of planar imaging implementations, namely (a) a setup used for fluorophore imaging (epi-fluorescence); (b) a setup to be used for fluorophore reconstruction in transillumination; and (c) another setup for fluorescence diffuse optical tomography.

In contrast to point monitoring devices, Fluorescence imaging systems can detect a fluorescence signal in large number of points. Thus, a two-dimensional image of an area of interest is created. A typical system comprises a camera together with a tunable filter, see FIG. 5*a*. A similar setup in transillumination is schematically illustrated in FIG. 5*b*. With a tunable filter the wanted detection wavelengths can easily be selected and a spectral resolution of approximately 20 nm wide may be achieved.

Fluorescence Imaging with Non-Linear Fluorophores

A particularly interesting subsection of fluorescence imaging is that of using non-linear fluorophores of the present embodiments. In the context of the present application, a "non-linear marker" is a luminescent marker, wherein a luminescence (L) of the marker is not linearly dependent on the luminous flow of excitation light (E). Non-linear markers thus have a luminescence according to: L=k*E^x, wherein x>1, and wherein k is a positive constant. The non-linear markers may also have a luminescence according to the following relationships: L=k*E^x+b, L=k(E)*E^x+b, L=k(E)*E^x+b(E), or L=k*E^x+b(E), where k and b are material constants that are either constant or depending on the local field of excitation light (E), i.e. for k(E) and b(E). In comparison to conventional luminescence imaging, non-linear markers (or fluorophores) may thus require more than one photons for excitation. This drastically decreases the excitation volume and provides a more localized excitation point. In this manner, contrast and resolution of luminescent imaging is improved, as is demonstrated below. In more detail, contrast and resolution of diffuse light in luminescent imaging of absorbing and scattering media is improved. Embodiments of the present invention take advantage of this effect.

Figure 16:
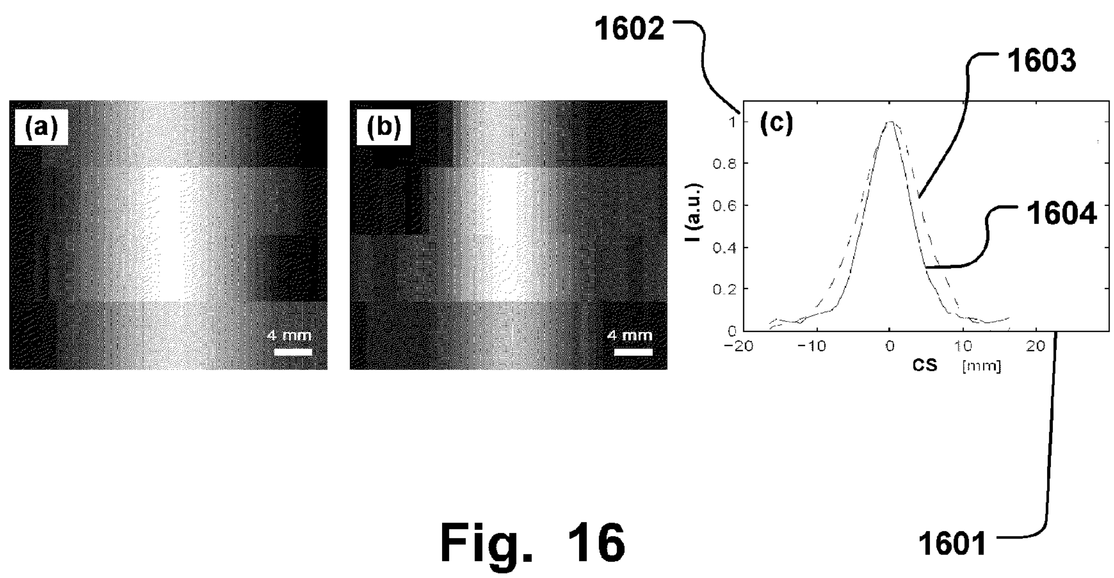
FIGS. 16A to 16C shows fluorescence images for a) linear conventional fluorescence dye and b) upconverting nanoparticles, and c) cross-sections of the images in a) and b).

To illustrate the difference between fluorescence imaging with linear and non-linear fluorophores, reference is made to FIG. 7*a-c*. FIG. 7*a* illustrates a linear fluorescence image in gray-scale. Each pixel (705) corresponds to one excitation point (704) in a grid pattern (701). FIG. 7*b* illustrates an image obtained with a two-photon, non-linear fluorophore, i.e. non-linear luminescent marker (702). In FIG. 7*c* the fluorophore (702) is shown in red (larger circle) (703), and the black dots (704) indicate the points of excitation in the grid pattern (701). The circle (703) corresponds to the projected image of the marker (702) on the grid pattern (701). The excitation points (704) corresponds to the positions of the light source, i.e. laser (503), when scanning the luminescent marker (702). It can clearly be seen that using the non-linear fluorophore increases contrast and resolution of the fluorescent image. This is further supported by FIG. 9 and FIGS. 10A,B described below. In particular, when the light source is in the position marked as 706 in FIG. 7*c*, close to the marker (702) or corresponding projected image (703) of the marker (702) on the grid pattern (701), the excitation volume is sufficiently small and localized to the light source position (706) for the non-linear marker, such that no luminescence is detected in the corresponding pixel (708) in FIG. 7*b*. For the linear fluorescence image in FIG. 7*a*, the corresponding pixel (707) receives luminescence due to the increased excitation volume in the scattering media. The two-photon non-linear dependence provides the narrow photon-density of the excitation volume. Thus, imaging the marker (702) based on the non-linear dependence of the detected luminescence on the excitation light intensity, the resolution may be increased. By making not an image of the fluorescence distribution itself, but rather of the florescence intensity for different excitation locations, images like in FIGS. 16(*a*) and (*b*) can be obtained. Since the excitation volume is smaller for the non-linear fluorophores, it will yield a smaller part of the fluorescent marker to shine and thus increase the resolution compared to conventional linear fluorophores.

Non-linear fluorophores require in general higher excitation intensities compared to linear fluorophores and some non-linear fluorophores even require coherent excitation. In scattering media, high intensities are difficult to achieve, since light cannot be focused, but rather spreads in every direction. This makes some non-linear fluorophores more suitable for fluorescence imaging in scattering media as compared to others. The fluorophores need to have an exceptionally high yield, and they may not require coherent excitation. Up-converting nanoparticles are one such non-linear fluorophore with high yield and non-coherent excitation.

Applications of Fluorescence Imaging

Fluorescence Tomography

A planar image of the fluorescence emitted from the surface of an object contains information about several aspects. The spectroscopic features yield the type of fluorophore, and the intensity is related to the concentration of the fluorophore.

This holds for fluorophores situated, or excited, on the object surface. Considering deeply situated fluorophores, the complexity increases manifold. This is due to the fact that the spectroscopic features as well as intensity are connected and affected by the optical properties of the object bulk tissue, i.e. surrounding tissue. Several factors must be considered, i.e.

Excitation light absorption and scattering. The fluorophore must be excited in order to emit light hence the excitation light must reach the fluorophore location.

Excitation light source position. A source positioned close to a fluorophore will excite the fluorophore more than compared to a source positioned far from the source, given the same excitation light.

Fluorophore position and size. Here the fluorophore is treated as an internal structured, i.e. a well-defined region containing a homogeneous distribution of fluorescent marker. Dependent on the size and position the emitted fluorescence will have different appearance on the boundary.

Emission light absorption and scattering. Emission is attenuated when it propagates through the tissue. Usually the optical properties for the emission are not the same as for the excitation light.

Emission light collection position. The collected intensity is dependent on where (on the boundary) it is detected. This is due to the inequality of the propagation path from the emission site (fluorophore position) and the collection site (boundary).

Due to the fact that these factors are connected in ever changing ways the need for tools to interpret the collected signals is inevitable. The fundamental goal in using optical tomographic techniques for fluorescence imaging of deeply situated fluorescent markers is then To quantify and localize a fluorophore within an absorbing and scattering object.

The term "quantify" means that the true concentration of a fluorophore is sought whereas the term "localize" means that the concentration in every three-dimensional voxel of the object is sought. The two terms also leads to the possibility to form a three-dimensional image, based on the fluorophore contrast, of the interior of the object hence motivating the use of the name tomography.

Applications of Fluorescence Tomography

Small Animal Imaging

Today, only Indocyanine green (ICG) has been granted FDA approval to be used on human patients for medical diagnostics but for small animal imaging the possible fluorophores are numerous. This is a result of the accelerated research within probe development over the past years triggered by the use of different microscopic techniques utilizing fluorescence for imaging biomedical phenomena in cells.

The fluorophores can be categorized into active probes and activateable probes.

The active probes are non-specific fluorophores that are attached to an affinity ligand specific for the target. These ligands can be antibodies, peptides and labeled small molecules. The active probe emits fluorescence upon excitation even if it is not attached to the target ligand. This results in background fluorescence which is non-specific, i.e. no information about the target to be imaged.

The activateable probes are more specific since these only emit fluorescence when "switched on". The fluorophores are arranged in close proximity to a quencher alternatively several fluorophores are placed together to self-quench each other. This arrangement is possible due to an enzyme-specific peptide sequence. In the presence of an enzyme the peptide sequence can be cleaved thus the fluorophores are free to emit light, no quenching. The use of activateable probes has been demonstrated for identification of proteases in vivo. The activateable probes are sometimes referred to as smart probes or optical beacons since they only are able to emit light upon excitation when the target molecule is present. Fluorescent probes are targeting a specific molecule or a specific biological event thus the function is imaged. This is in contrast to other non-targeting fluorescent dyes, e.g. ICG, which are used to visualize vascularization and permeability. Another way of increasing the contrast is to use probes that are genetically encoded. A transgene (reporter gene) is inserted in the cell. The transgene encodes for a fluorescent protein (FP) which upon transcription will be produced intrinsically inside the animal. The probes can be detected using optical techniques and this modality is called indirect fluorescence imaging since the fluorescence emitted visualizes the presence of gene regulation or gene expression. Cells can be transfected with a reporter gene and cell tracking can be imaged. Fusing the FP to a gene of interest makes it possible to image almost any protein in vivo. The FPs in indirect fluorescence imaging provides interesting imaging capabilities e.g. protein-protein interactions due to the fact that the protein of interest might be unaffected while the FP emits fluorescence.

There exist several types of fluorescent proteins but the main family is based on green fluorescent proteins (GFP). The probe development is pushing forward to develop GFP emitting and absorbing in the NIR region. Today no NIR FPs is present but yellow and red fluorescent proteins have been reported (YFP and RFP). The contrast is dependent on the fluorophore concentration and the fluorophore position. The contrast is also controlled by so called active probes. If the fluorophore is not active no fluorescence will be emitted. An ever present problem using fluorescence diagnostics in biological media is autofluorescence and the background fluorescence.

Autofluorescence is the fluorescence emitted by endogenous chromophores while the background fluorescence is fluorescence originating from fluorescent probes outside the region-of-interest. Ways of theoretically subtract the autofluorescence and the background fluorescence has been reported. The presence of non-specific fluorescence effectively reduces the contrast.

Clinical Cancer Diagnostics

The main application so far is breast cancer diagnostics using ICG or derivatives of the same. Fluorescent proteins is evidently not an alternative for human applications hence fluorophore imaging will be achieved by functionalizing non-specific molecular probes.

Non-Linear Fluorophore Tomography

Due to the quadratic dependence of the emitted fluorescence in e.g. up-converting nanocrystals, the fluorescence tomography is improved.

Figure 9:
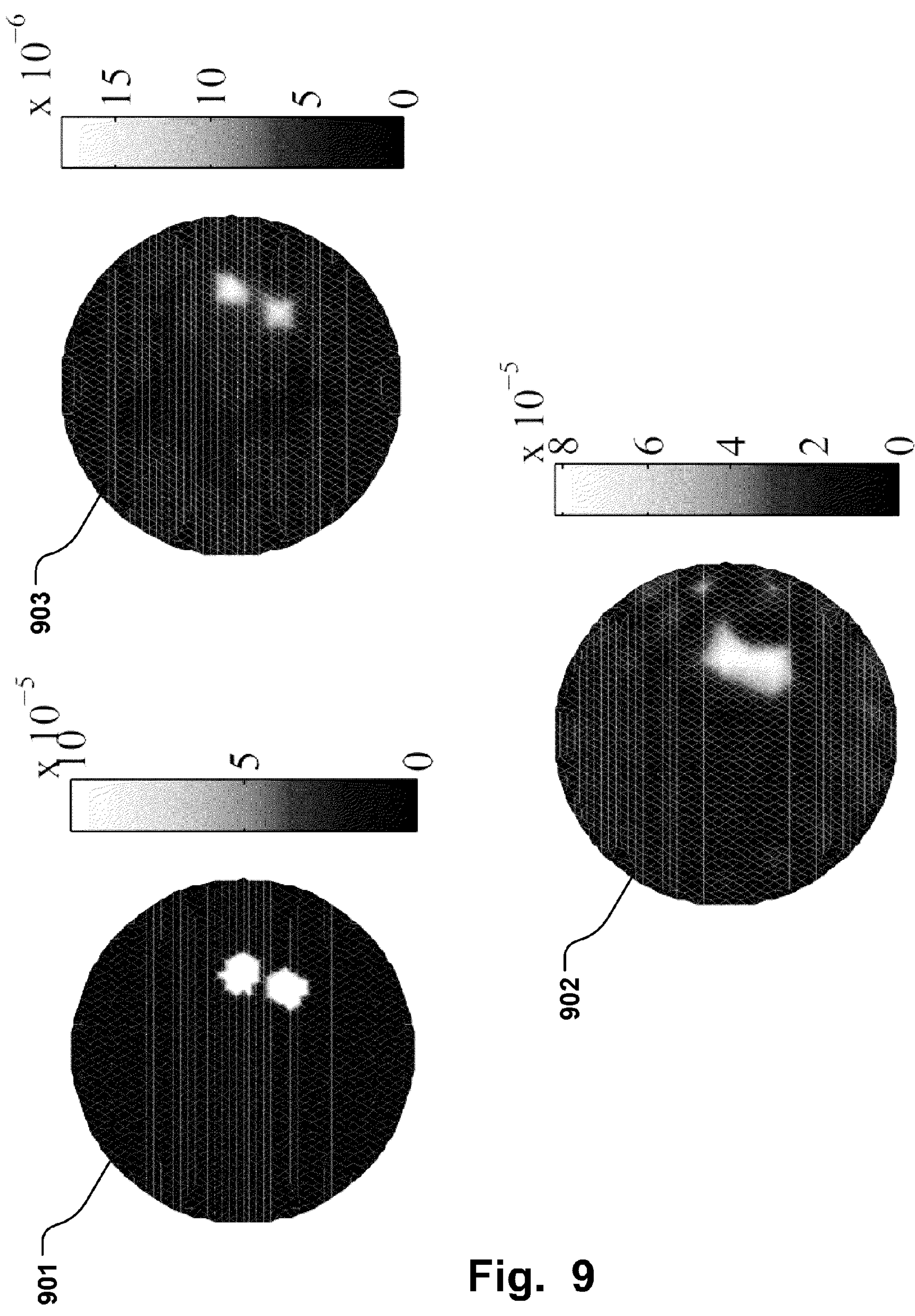
FIG. 9 shows a comparison of tomographical reconstructions between a linear and a non-linear fluorophore.

FIG. 9 depicts the differences between using a linear fluorophore and a quadratic fluorophore.

Figure 8:
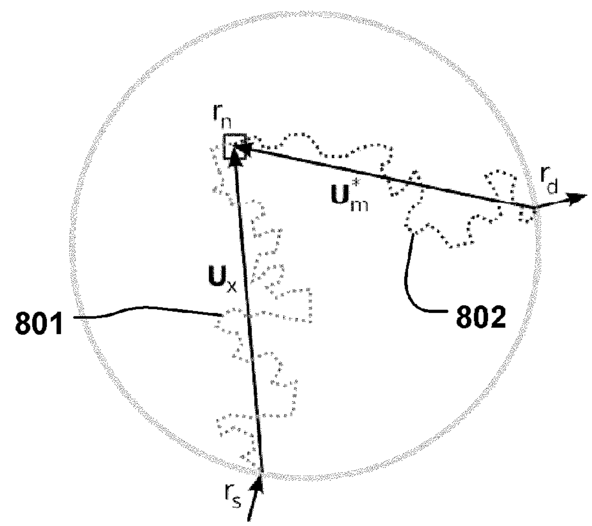
FIG. 8 is a schematic illustration of excitation and emission light propagation in a scattering medium.

FIG. 8 is a schematic illustration of excitation (801) and emission (802) light propagation in a scattering medium.

Figure 11:
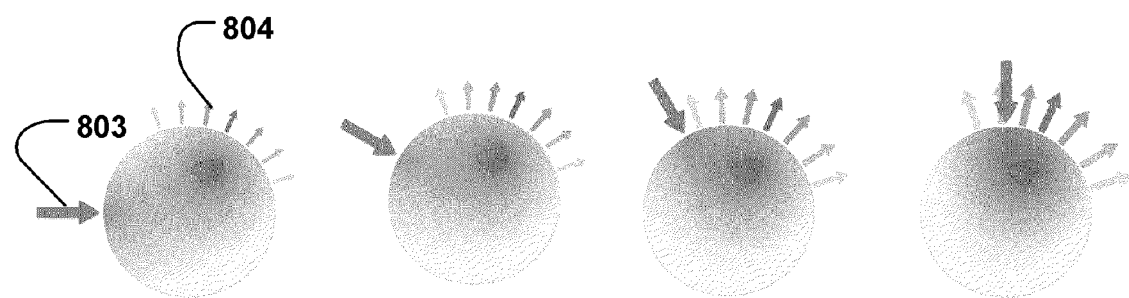
FIG. 11 is a schematic illustration of the fluorescence tomography problem.

FIG. 11 is a schematic description of the fluorescence tomography problem. An excitation source emitting excitation light (803) is translated on the boundary whereas the emitted fluorescence (804) is static in position while the emission intensity is changing dependent on the source location.

Figure 10A:
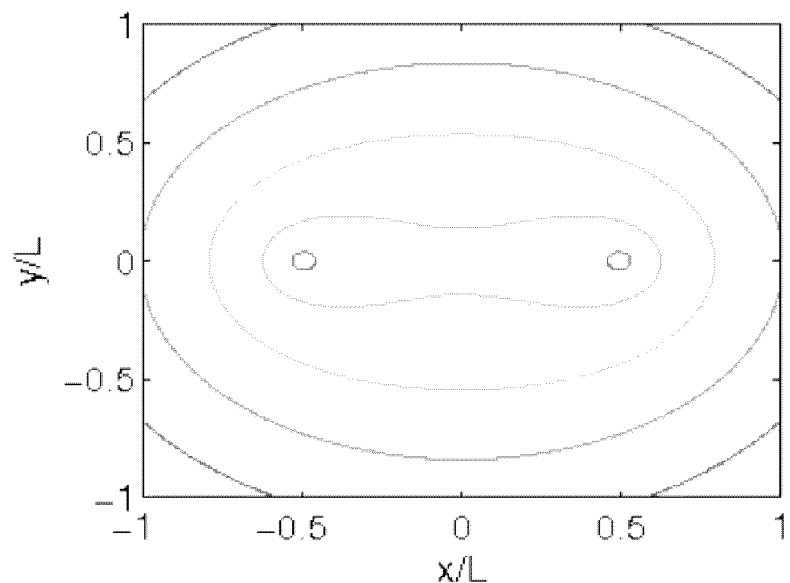
FIGS. 10A and 10B show sensitivity profiles for fluorophores having linear (10A) and quadratic (10B) power dependence.
Figure 10B:
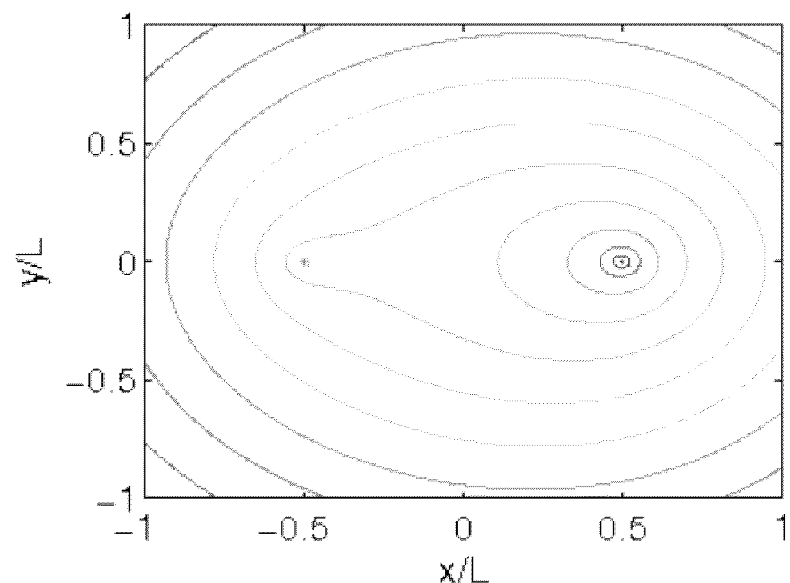

FIGS. 10A and 10B show sensitivity profiles for fluorophores having linear (10A) and quadratic (10B) power dependence. The source is on the left in the figures, and the distance to the detector is L. The calculations were performed using the analytic expression for the Green's function for an infinite homogenous medium. As seen in the FIGS. 10A and 10B, the quadratic sensitivity profile is very sharp in the vicinity of the light source, around a symmetrical revolution around the x-axis. This implies that it is possible to extract information with higher sensitivity (resolutions) in one plane.

In other embodiments of non-linear fluorophores of higher order, e.g. cubic fluorophores, the contrast enhancement is even further improved (not shown).

Tissue Optics and Autofluorescence of Tissue

Within the field of tissue optics, light interaction with tissue is studied. Optically, biological tissues are inhomogeneous and absorptive media, with a slightly higher refractive index than water. When light interacts with tissue, multiple scattering and absorption events are expected to occur, where the possibilities for these events are highly wavelength dependent. Since tissue has a high concentration of water, it is an advantage to use light from a wavelength region where the absorption from water is low, this will enforce an ultimate limit on the usable wavelengths. However, in transdermal non-invasive applications, as in certain embodiments, light needs to penetrate the skin which will put further constraints on the usable wavelengths.

The skin can be seen as a layered structure, with the stratum corneum on top, followed by the epidermis and the dermis below. The stratum corneum and epidermis are very effective in attenuating light, mainly due to high absorption for wavelengths <300 nm from aromatic amino acids, nucleic acids and urocanic acid. For longer wavelengths, 350-1200 nm, melanin in the epidermis is the major absorber. As light enters the dermis, scattering begins to dominate over absorption. The dermis can thus be described as a turbid tissue matrix. For tissue types below the dermis, scattering usually dominates over absorption. In a crude approximation, the scattering can be modeled using Rayleigh scattering. This implies that light at shorter wavelengths will be much more scattered than light at longer wavelengths.

Considering both the scattering and the absorption in tissue, the transdermal diagnostic window resides in the longer wavelength regions and can be considered to range from 600 nm to 1600 nm.

Tissue contains several endogenous fluorophores which have a strong fluorescence with small Stokes shift when excited by $\lambda<600$ nm. For longer wavelengths in the diagnostics window, the endogenous autofluorescence from tissue is in general much weaker. However, in many imaging and tomography applications, the signal itself is also weak, thus still limited by the background autofluorescence which causes artifacts. A typical signal (continuous line) with an autofluorescence background spectrum (dashed line) is shown in FIG. 1.

Figure 1B:
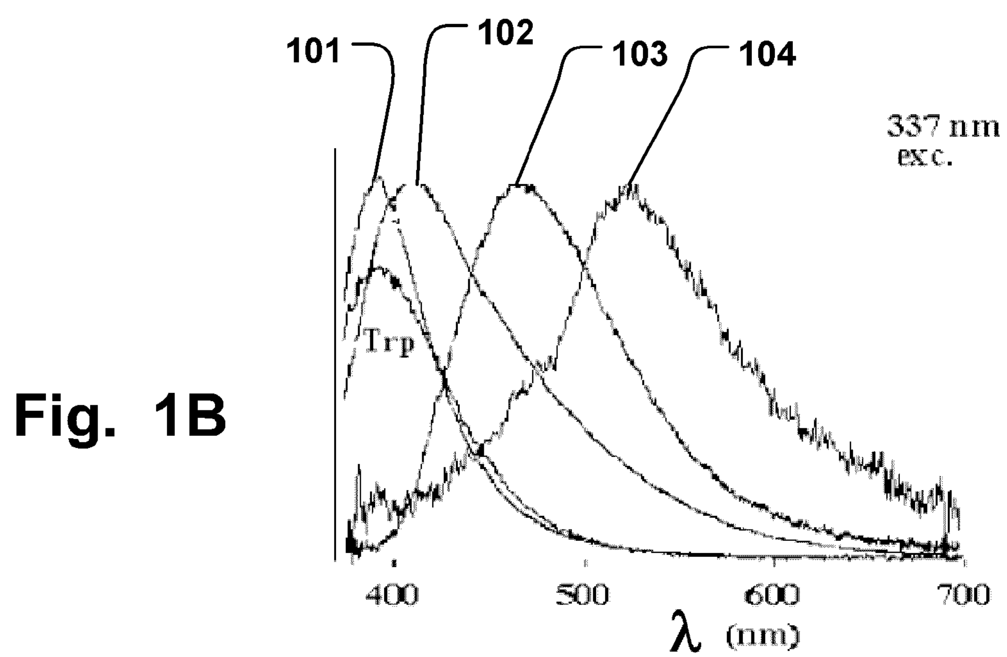
FIG. 1B is a graph showing fluorescence spectra from some tissue fluorophores.

The aforementioned autofluorescence, or the tissues own endogenous fluorescence, is caused by several different fluorophores. Some of the common tissue fluorophores are collagen and elastin present in connective fibres, tryptophan present in most proteins and flavins and nicotinamid adenine dinucleotide (NADH) active in the digestion of cells, see FIG. 1B showing spectra of collagen (101), Elastin (102), NADH (103), and caroten (104).

The spectra are also influenced by the optical properties of the tissue. Strong absorbers, such as haemoglobin, can absorb fluorescence light at certain wavelengths and thus change the appearance of the fluorescence spectrum, creating false dips and peaks.

Haemoglobin may also decrease the overall intensity of the fluorescence spectrum, without changing its shape, by absorbing the excitation light.

Exogeneous Fluorophores

Some examples for exogenous fluorophores are fluorescent proteines (FP), NIR-dyes (ND), Quantum dots (QD), or Photosensitizers (PS).

Quantum dots are a linear fluorophore that emits a signal that is more Stokes shifted than the tissue autofluorescence. Quantum dots are fluorophores that absorb mainly in the ultraviolet (UV) region. Since using illuminating light at short wavelengths is not ideal for transdermal measurements and UV light is subject to shallow transdermal penetration depths and risks for DNA damage in the illuminated tissue, QD are not suitable for many applications. Furthermore, quantum dots are often fabricated of materials that are highly toxic for organisms. Moreover, studies have shown that quantum dots tend to react when exposed to biological environments and can be very harmful.

Non-Linear Fluorophores

Examples for non-linear fluorophores are nanoparticles (NP), described in more detail below.

Upconversion

Upconversion is a non-linear process that occurs when two or more photons are absorbed and a photon of higher energy, than those of the incoming photons, is released.

The process is for instance observed in materials containing a meta-stable state that can trap one electron for a long time, increasing the interaction-probability with another arriving photon.

In some embodiments, luminescent markers in form of solids doped with different rare earth ions are used to obtain upconversion.

Solid state upconverting materials are for instance fabricated by doping the materials with rare earth ions. The rare earths fills their outer electron shells before their inner shells, giving them sharp atomic-like spectral lines, even when bound in solid materials.

Upconversion can happen due to numerous processes, which impact the upconversion process differently depending on the ion pairs and the excitation intensities.

Figure 2:
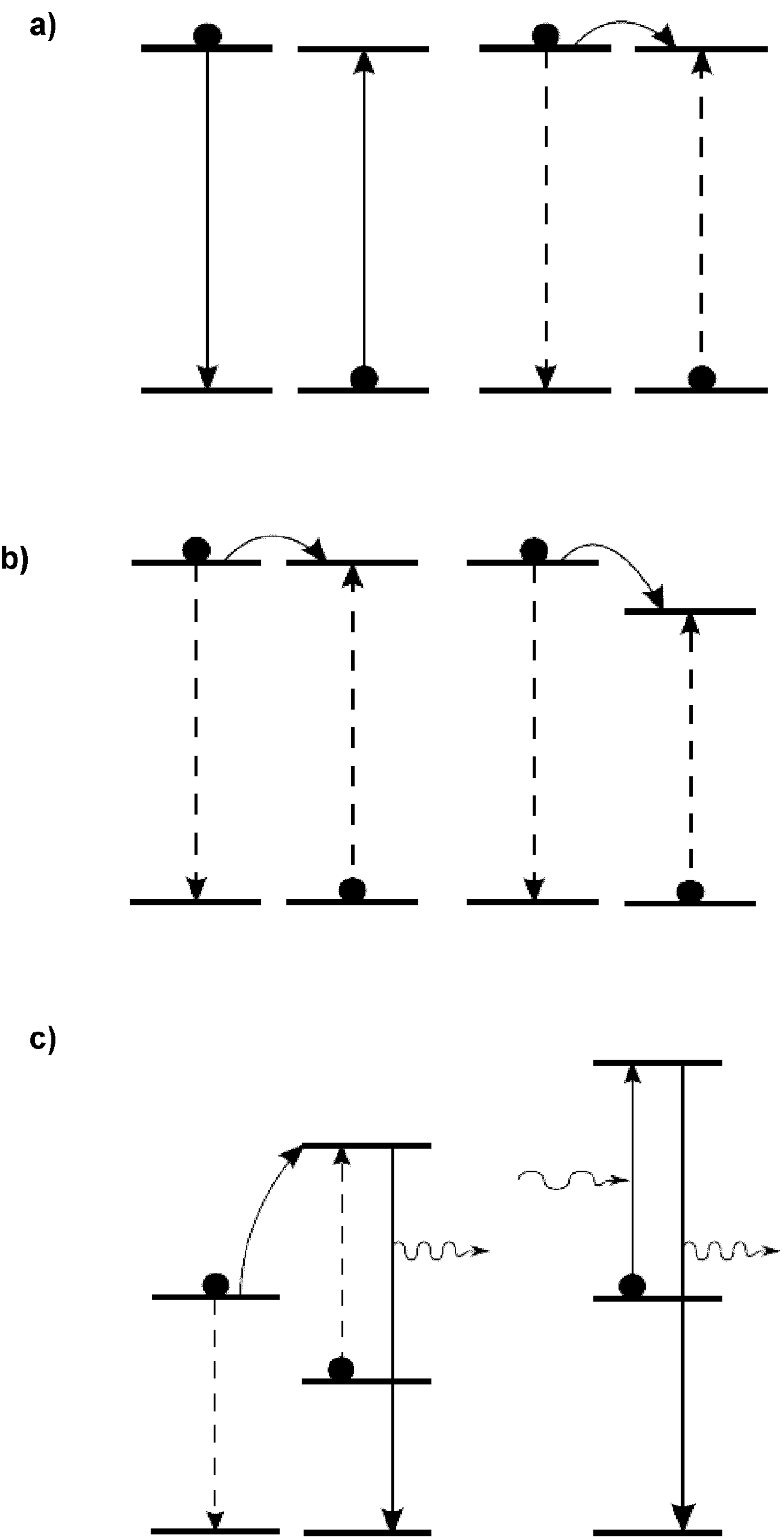
FIGS. 2a)-c) are schematic illustrations of a) radiative and nonradiative energy transfer; b) Resonant and nonresonant energy transfer; and c) Comparison of ETU (left) and ESA (right) upconversion.

Some upconversion processes are illustrated in FIGS. 2*a*)-*c*). Some of the processes involve energy transfer between ions. This energy diffusion, can be radiative or non-radiative, resonant or non-resonant, see FIG. 2*a* and FIG. 2*b*. In the radiative case, a photon is released from the sensitizer and absorbed by the activator, while in the non-radiative case, the excitation energy will jump from one ion to the other via an electrostatic interaction. The two cases can be experimentally distinguished. The radiative transfer is dependent on the shape of the sample and also affects the emission spectrum as well as the lifetime of the activator. When the transition is non-resonant, it has to be phonon-assisted. The non-resonant transitions are encountered for higher energy differences between rare-earth ions compared to other solid materials, especially in the non-radiative case.

Furthermore, Energy Transfer Upconversion (ETU) and Excited-State Absorption (ESA) processes are illustrated in FIG. 2*c* on the left respectively on the right of the Figure. Excited state absorptions happen when an ion, being in an excited state, absorbs one more photon. The probability for this process is usually small, and can only be observed under coherent pumping. Energy Transfer Upconversion is a process involving energy transfer between ions. Here, an activator in an excited state is considered. Energy can then be transferred non-radiatively from a sensitizer. This is possible because only energy differences are significant in preserving the energy.

Figure 3:
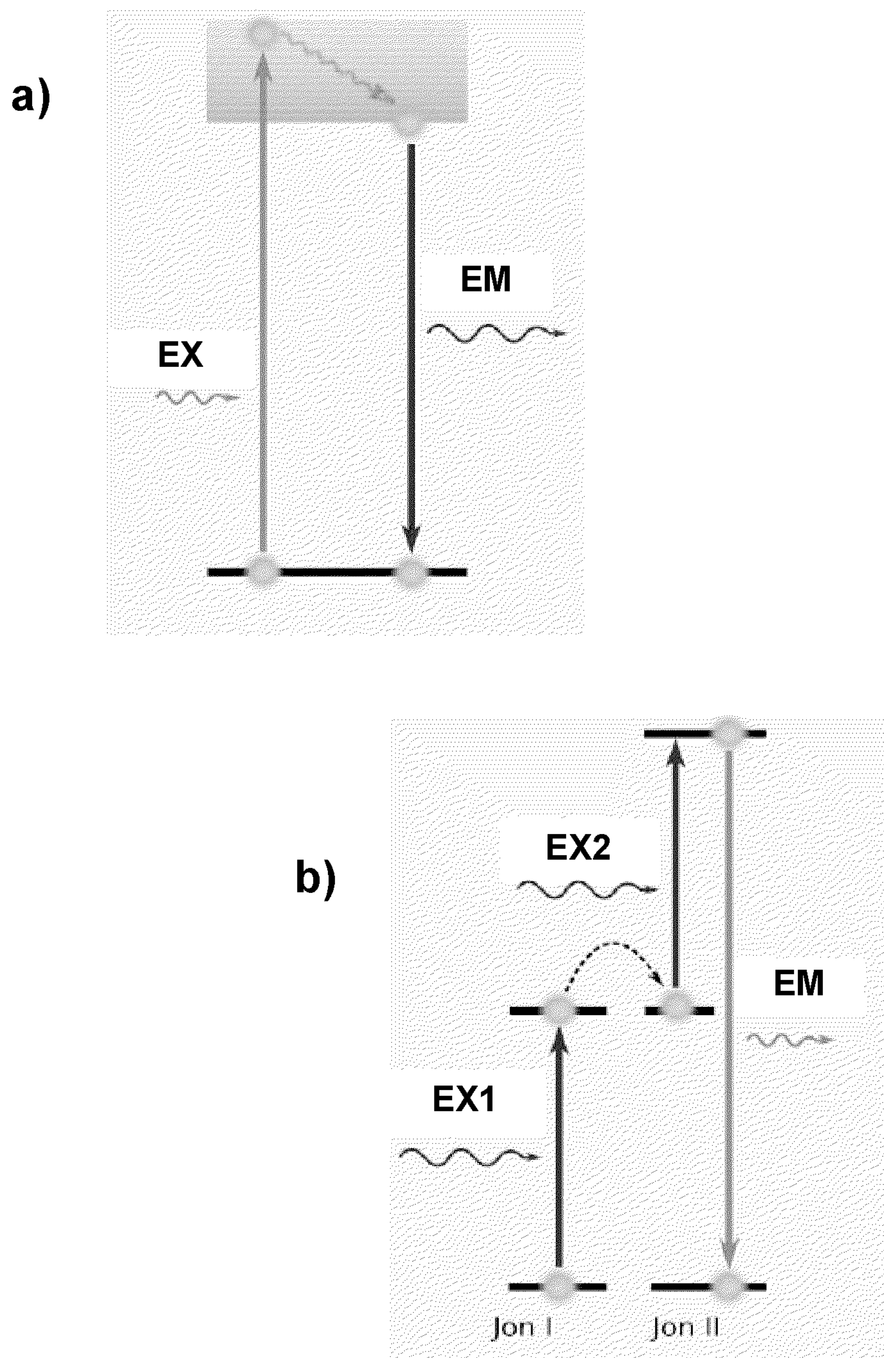
FIGS. 3a) and b) are schematic illustrations of a) single excitation fluorescence, and b) multiple excitation in upconversion fluorescence.

FIGS. 3*a*) and *b*) are schematic illustrations of fluorescence and multiple excitation in upconversion luminescence, respectively. In FIG. 3*a*) the emission wavelength (EM) is longer than the excitation wavelength (EX). FIG. 3*b*) shows multiple excitation occurring in step 1 (EX1) and step 2 (EX2), where the emission wavelength (EM) is shorter than the excitation wavelengths.

Nanosized Upconverting Crystals

Upconverting nanocrystals are herein disclosed as fluorophores in biomedical imaging applications due to their unique property to efficiently emit anti-Stokes shifted light upon near-infrared (NIR) excitation. This provides for detecting a fluorescent signal in a region where no autofluorescence is present.

Nanosized upconverting particles are for instance lanthanide doped oxides ($Y_2O_3$), which are easy to fabricate.

Other nanosized upconverting particles are for instance fluorides, which have higher efficiencies than $Y_2O_3$. The higher efficiencies can be explained by the low phonon energies in fluorides, which lower the probability for non-radiative decay.

Further nanosized upconverting particles are for instance made of sodium yttrium tetrafluoride ($NaYF_4$), co-doped with either $Yb^{3+}/Er^{3+}$ or $Yb^{3+}/Tm^{3+}$.

$NaYF_4$ can crystallize in two phases, cubic or hexagonal, called α-NaYF4 and β-NaYF4, respectively. The upconverted luminescence from the β-phase material is approximately one order of magnitude higher compared to the upconverted luminescence from the α-phase. Currently, it is also possible to fabricate nanosized particles in either the cubic or hexagonal phase.

Disregarding the efficiency differences, the particles also show other size-dependent properties. For example, the ratio between the different emission lines is different for nanoparticles and bulk material.

Because of their unique optical properties, upconverting nanoparticles are suitable as biological markers for different bioimaging applications. There are cheap laser diodes at the excitation wavelength of 980 nm, which is a very suitable wavelength for bioimaging applications since the light penetrates relatively deep in tissue, which lowers the risk of photodamage.

With upconverting nanocrystals, luminescent imaging does not suffer from any autofluorescence. Luminescent imaging is provided with better contrast, e.g. compared to biological markers of Stokes-shifted fluorophores.

In addition, the non-linear fluorophores, such as the upconverting nanoparticles may also be biofunctionalized, giving them for example tumor seeking abilities.

The non-linear fluorophores may be water soluble, allowing for easy administration in certain applications, such as in solutions for intravenous, peroral, or enteral administration.

A way to provide upconverting nanoparticles as water soluble, is to coat the particles with a structure that is polar. Coatings may for instance be made of polymers or silica. Both synthetic polymers, for example, Polyethylene glycol (PEG), and natural polymers may be used for the coating. These polymers are stable in biological environments and do not interfere with the optical properties of the nanocrystals in any significant negative way.

Coating the particles with silica usually gives a very robust coating, which is in particular advantageous in biological environments.

Water soluble upconverting nanoparticles may be provided without coatings. Hydroxyl groups may be attached to the surfaces of the upconverting nanoparticles, either by chemical bonds or physical absorption. Hydroxyl groups are by definition formed by covalent binding, and the final structure has polar properties.

In addition, a stable protective coating may be applied to the nanoparticles for making them advantageously suitable for use in biological environments.

Functionalization

Functionalization of the upconverting nanoparticles may be made in similar ways than functionalizing quantum dots, such as described in X. Gao et. al., In vivo cancer targeting and imaging with semiconductor quantum dots, Nature Biotechnology, 22, 8:969-976, 2004, which is incorporated herein in its entirety for all purposes. In Gao et. al. methods are described that are applicable on upconverting rare-earth doped nanoparticles.

Figure 4A:
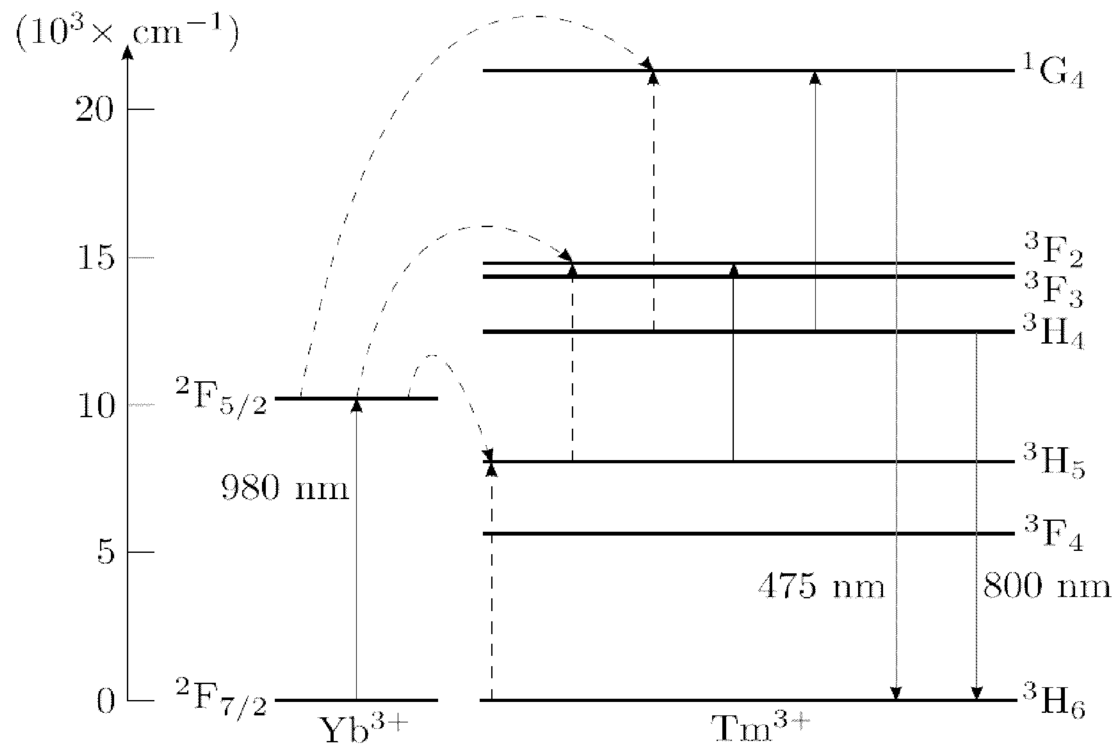
FIG. 4A is a schematic illustration of an upconversion processes in the $Yb^{3+}$-$Tm^{3+}$ ion pair of a upconversion nanocrystal.
Figure 4B:
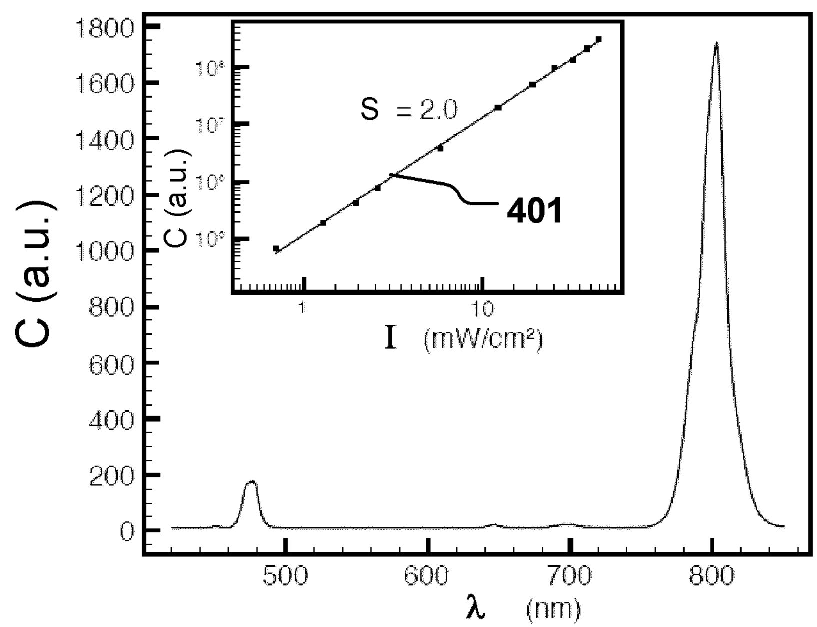
FIG. 4B is a graph showing the emission spectrum for the upconversion nanocrystals of FIG. 4A.

The upconverting nanoparticles used in an embodiment in this disclosure were $NaYF_4$-crystals prepared according to the method described in G. Yi et. al., Synthesis, characterization, and biological application of size-controlled nanocrystalline $NaYF_4$:Yb,Er infrared-to-visible up-conversion phosphors. Nano Letters, 4, 11:2191-2196, 2004, doped with a combination of $Yb^{3+}$ and $Tm^{3+}$. The energy diagrams for the two ions are shown in FIG. 4A. FIG. 4A is a schematic illustration of upconversion processes in the $Yb^{3+}/Tm^{3+}$ ion pair. Nonradiative upconverting processes are illustrated with dashed arrows and non-radiative decays are omitted for clarity. FIG. 4B is a graph showing the emission spectrum for these upconverting nanoparticles. The blue emission line at 477 nm is only visible for higher pump intensities. The pump-power dependence of the 800 nm line was measured to be quadratic using low intensities, as seen in the inset of FIG. 4B, showing intensity (I) on the x-axis and counts (C) on the y-axis and where the slope (S) of the fitted line (401) equals 2.

In an embodiment, the non-linear markers are attached to an imaging contrast agent for another imaging modality. For instance a non-linear marker is attached to a contrast agent for imaging with a conventional imaging modality, such as Magnetic Resonance Imaging (MRI), X-Ray, etc. In a specific embodiment, a non-linear marker is attached to an organic gadolinium complex or gadolinium compound, which has paramagnetic properties. When used as an MRI contrast agent, contrast is enhanced in medical magnetic resonance imaging. At the same time, luminescence imaging or tomography may be made, providing for functional diagnostic information combined with high resolution MRI of one and the same region of interest and in-vivo.

Other applications are provided in non-biological areas. Examples for such areas are luminescent imaging or tomography for material testing, including quality control of tablets, filters for liquids or gases through which flows a medium with non-linear markers, etc.

Experiments

Upconverting nanocrystals were used in experimental set-ups in order to confirm the applicability of non-linear markers in luminescent imaging. To demonstrate the adequacy for use as fluorophores for in vivo applications, two experiments were performed.

Firstly, the differences in contrast using traditional down-converting fluorophores and quadratic fluorophores in the form of upconverting nanocrystals were demonstrated.

Secondly, simulations performed for tomographic reconstruction using non-linear fluorophores, such as quadratic fluorophores in the form of upconverting nanocrystals, were performed.

The planar imaging systems used for data collection are shown schematically in FIGS. 5*a* and 5*b*. FIG. 5*a* is a schematic illustration of a setup for fluorophore imaging (epi-fluorescence); and FIG. 5*b* is a setup for fluorophore reconstruction in transillumination.

A tissue phantom (501) was used that consisted of a solution of intralipid ink with optical properties determined by a time-of-flight spectroscopy system (500). The fluorophores (502) were contained in capillary tubes with inner diameters of 2.4 mm. The concentrations of the fluorophores were 1 wt % for the nanoparticles and 1 μM for the traditional down-converting fluorophores of the type DY-781.

The concentration of the nanoparticles was chosen to have a reasonable correspondence with studies using quantum dots, namely a concentration of 1 wt % was used.

Figure 7:
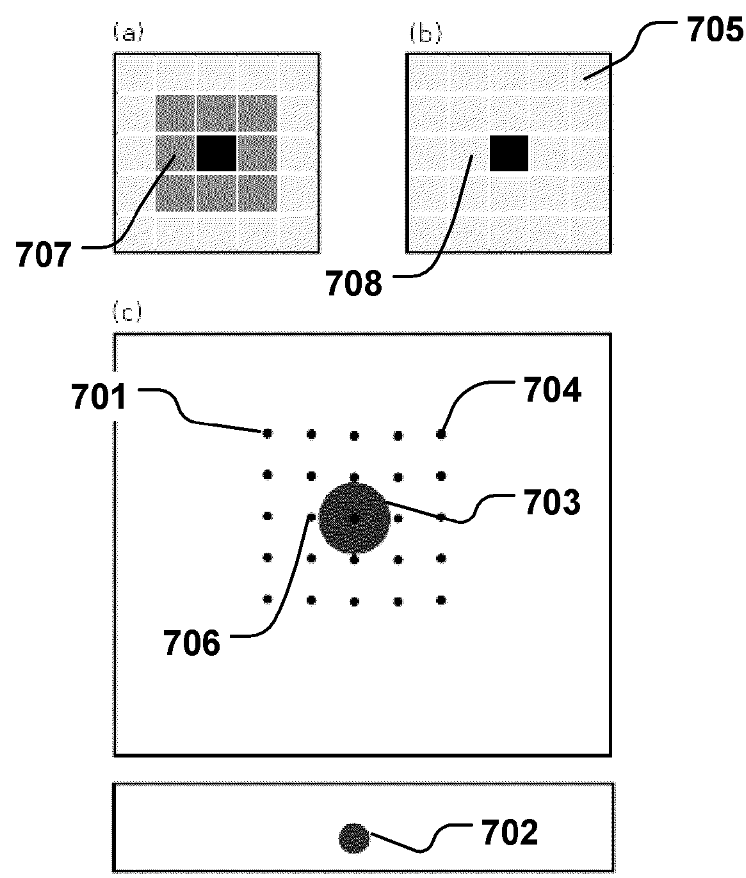
FIGS. 7a) to c) are schematic illustrations of the difference between fluorescence imaging with linear and non-linear fluorophores.

Using two step motors from a CNC machine, the fiber coupled lasers (503) could be raster scanned. The positions of the laser in the raster scan may be described by a grid pattern (701) as shown in FIG. 7. An image was acquired for each scanned position with an air cooled CCD (504) camera sitting behind two dielectric band pass filters centered at 800 nm. FIG. 5*c* shows a raster scanning setup (507) where the laser is scanning the tissue phantom (501) from a below position (505). The CCD (504) may capture one image for every position (506) of the laser. The positions (506) describes a grid pattern (508) similar to the grid pattern (701) in FIG. 7. For each position (506) of the laser, the emitted fluorescence from the entire side of the phantom (501), i.e. the total luminescence intensity, was measured and summed to make up one pixel in the resulting image. Hence the number of pixels in the image was given by the number of excitation positions (506) and not by the number of CCD pixels. The resolution may thus be determined by the photon-density of the excitation light from the laser light source (505), and not by the photon-density of the fluorescence emission light. In this way, because the two-photon photon-density in the excitation volume is more narrow than the single-photon photon-density, the resolution could be increased. When summing the total luminescence intensity a threshold value may be applied to the detected luminescence. In this way resolution may be increased. For example, only if the luminescence intensity is above a defined threshold it will be added to the total luminescence intensity. The threshold may be defined as a value in the CCD (504), for example if the luminescence intensity is below 30% of a peak value it will be discarded, as it might be considered as a background signal. Further, if the resulting total luminescence for a pixel, or position (506) of the laser, is below another threshold value it may be considered as background signal and removed. Alternatively, the quadratic intensities of the luminescence signal may be summed. In this way the resolution may be further increased. For example, the luminescence intensity detected by the CCD (504), which may have relative value between 0 and 1 by definition of a peak intensity value in the CCD, may be multiplied with itself before added to the total luminescence intensity for the current pixel or position (506). Further, the total luminescence intensity may be multiplied with itself for each pixel or position (506). FIG. 16A to 16C shows images using the scanning imaging technique, where each pixel in the images corresponds to the fluorescence induced by a single excitation point, i.e. light source position (506). FIG. 16A shows the image for a linear conventional fluorescent dye, and FIG. 16B the image from nonlinear upconverting nanoparticles, with a comparative cross-section profile in FIG. 16C displaying the FWHM as 10.5 mm and 8.0 mm respectively, giving an improvement of a factor of 1.3.

Autofluorescence Insensitive Fluorescence Molecular Imaging

The epi-fluorescence setup was used for this experiment. The optical properties of the phantom was chosen to be μ's=6.5 cm-1 and μa=0.44 cm-1 at 660 nm, which fall into the range of those found in small animals.

The capillary tubes containing the fluorophores, DY-781 and $NaYF_4$: $Yb^{3+}/Tm^{3+}$, were submerged to a depth of 5 mm, where the depth was taken as the distance from the front surface of the tubes to the surface of the phantom. DY-781 was chosen in order to get a fair comparison, since it emits at 800 nm too and has a quantum efficiency on par with more commonly used dyes, for example the rhodamine class.

Two diode lasers were used to excite the fluorophores. DY-781 was excited at 780 nm, and the nanoparticles were excited at 980 nm.

The lasers were raster scanned over an area of 4.4×4.4 cm2 consisting of 121 positions. The images were then summed, giving a representation of the photon distribution on the surface. This, provides whether or not a fluorescent inclusion can be detected. In order to suppress the effects of bad pixels on the camera, a median filter with a kernel of 3×3 pixels was applied to the summed images. To simulate autofluorescence, DY-781 was added into the phantom up to a point where the contrast was so poor that the data could not be used in a sensible way.

Illumination intensities that were used were deemed non-harmful to tissue. The final used excitation light had a spot size of 1 $cm^2$ from both lasers on the surface of the phantom, giving intensities of 40 $mW/cm^2$ for the 780 nm laser and 85 $mW/cm^2$ for the 980 nm laser.

Figure 6:
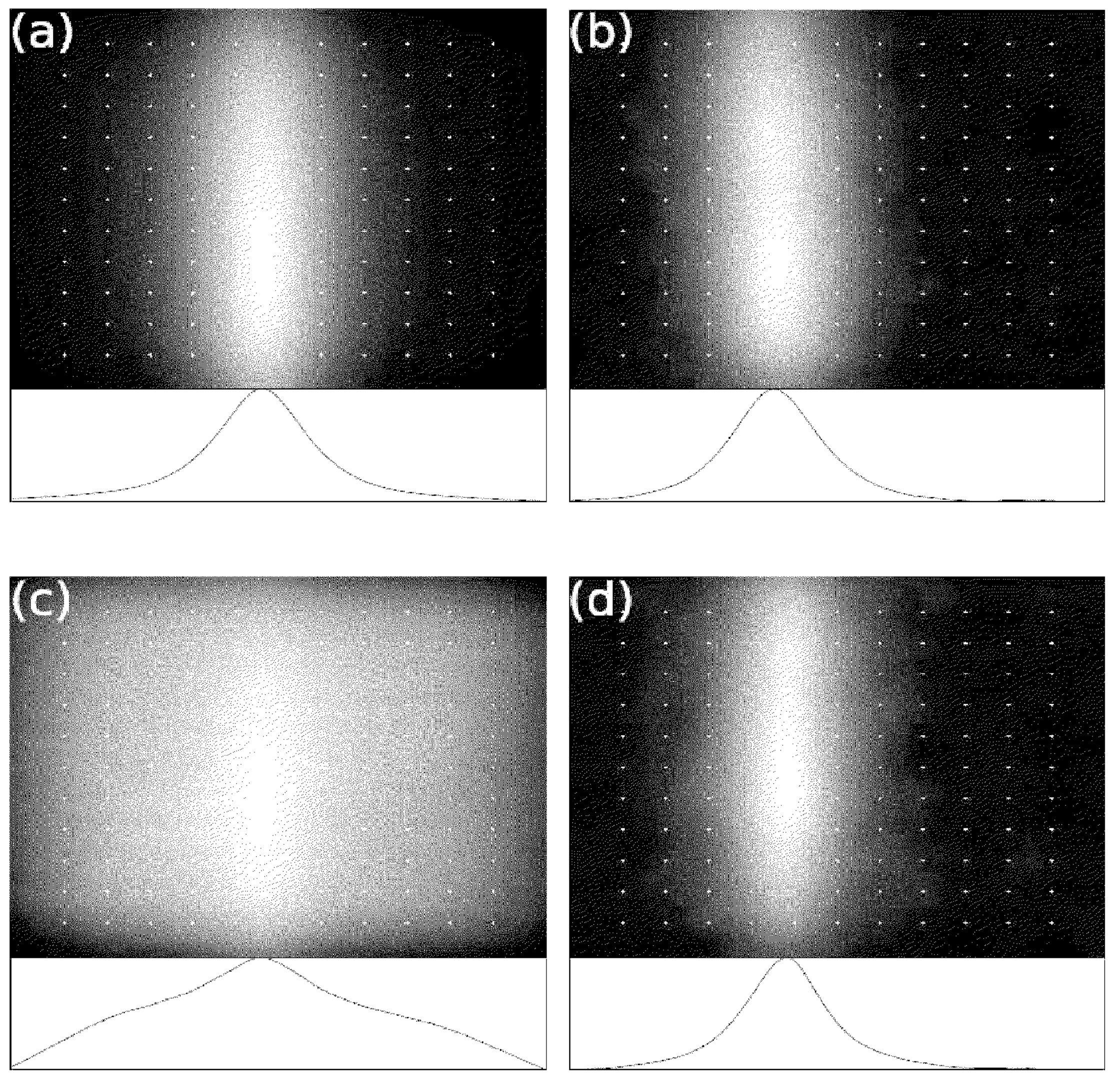
FIGS. 6a) to d) are images and graphs showing various fluorescence intensity distributions.

FIGS. 6*a*) to *d*) are images and graphs showing various fluorescence intensity distributions resulting from the experiment. In more detail, comparative images are shown with respect to the DY-781 dye, seen in FIGS. 6(*a*) and (*c*), and the nanoparticles, seen in FIG. 6(*b*) and (*d*), with and without autofluorescence, along with plots showing the sums in the vertical directions, respectively. The white dots in the images have been added artificially and represent the positions used for the excitation light. The left column shows the results using DY-781, and the right column shows the results using upconverting nanoparticles.

The images shown in FIGS. 6(*a*) and 6(*b*) are taken without any added autofluorophores, wherein the images shown in FIGS. 6(*c*) and 6(*d*) are taken with a background autofluorophore concentration of 40 nM.

In more detail, FIGS. 6*a*) to *d*) show the images taken with and without autofluorescence along with their cross section profiles.

As can be seen from FIG. 6(*d*), there is reduced autofluorescence background in comparison to FIG. 6(*c*), improving the signal-to-background contrast for the upconverting nanoparticles. These figures clearly demonstrate the contrast difference using downconverting fluorophores and upconverting nanocrystals. It is worth to notice that even without any artificial autofluorophores added, the intralipid itself autofluoresces and the effect is visible in the cross section profile in FIG. 6(*a*).

The end result using the nanoparticles is mainly limited by the signal-to-noise ratio of the detector. This means that by increasing the excitation power, it is possible to enhance the obtainable image quality.

The situation is different for the DY-781 dye. The dye is very efficient, and is in general not limited by the signal-to-noise ratio. However, it is limited by the signal-to-background contrast. This means that an increase in excitation power will not result in a better image quality.

Fluorescence Molecular Tomography (FMT)

Simulations of FMT using non-linear fluorophores and traditional fluorophores were performed in transmission-fluorescence setups, as shown in FIG. 5*b*. The simulated tissue phantom was modeled as a semi-infinite cylinder (508) with a radius of 43 mm. The optical properties were μ's=10 cm-1 and μa=0.4 cm-1 at λ=660 nm, with 16 uniformly spaced source-detector points (509) around one plane of the geometry. The fluorophores were placed closely together as sticks extending throughout the phantom as shown in FIG. 5*b*.

The forward model used a uniform mesh consisting of 1785 nodes. For the reconstructions, a pixel basis of 17×17 pixels was used. There are several strategies for choosing reconstruction bases. Two examples are the second-mesh basis and the pixel basis. All strategies, however, aim to reduce the number of unknowns in the problem. This is motivated since the solution is expected to be smooth and using a coarser basis improves the ill-posedness. In this experiment the pixel basis was chosen, which is a set of regularly spaced pixels. This basis is suitable for problems with no spatial a priori information.

The input data for the reconstruction were obtained from a forward simulation. The sources were modeled as isotropic point sources radiating with 1 W situated at a distance of one scattering event inside the phantom.

The procedure for the reconstruction may be briefly considered as performing the following steps; i) For each of the excitation positions: calculate the excitation field with a correct power factor; ii) For each detection position: calculate the emission field with the aforementioned excitation field, i.e. the adjoint-method; iii) calculate the product between the excitation field and the emission field (adjoint) for each excitation and detection pair. That is, calculate N*M, where N is the number of excitation positions and M the number of emission positions. The latter can be considered as the calculation of the sensitivity profiles. The resulting internal distribution is stored. iv) Find the internal fluorophore distribution which best describes the what is detected, for example by solving least-square problem by minimizing $\|Ax-y\|$, where A is a matrix containing the sensitivity profiles, x the internal distribution of fluorophores, and y the measured data.

For non-linear markers the non-linear dependence of the light propagation (emission and excitation) may be modeled for example by solving the related diffusion equation or use Monte-Carlo simulations. This may be essential in order to utilize the non-linear markers for tomography. When having calculated the excitation field it may be used as input data to the emission problem. At one of the aforementioned steps for the tomography reconstruction the power dependence of the marker may be considered. For example, for non-linear markers having a specific power dependence of the luminescence (L) on the excitation light (E), the field strength of the excitation field is raised to the same power, i.e. calculating the quadratic product of the excitation field if the non-linear marker has a quadratic power dependence. The quadratic excitation field strength is the used as source term for calculating the emission field in the emission problem. This may result in a more narrow sensitivity profile and thereby increased resolution. The narrow sensitivity profile corresponds to the narrow or small excitation volume previously addressed. Hence, reconstructing a tomographic image of the luminescent marker may comprise calculating a product of the excitation field according to the non-linear dependence, where the calculation of the emission field is based on this product. And calculating the product may comprise multiplying the field strength of the excitation field so as to form a product of the field strength raised to the power corresponding to the power dependence of the non-linear relationship.

The accuracy of the reconstruction is dependent on how much information, such as detected luminescence, is obtained, for each light source position when the light source is moved in relation to the luminescent marker, or the vice versa. In addition to obtain the reconstruction information by spatial variations, a multiple of excitation wavelengths and emission wavelengths of the luminescent marker may be used to obtain the reconstruction information by instead spectral variation. The CCD may in this situation detect luminescence of several wavelengths for utilization in both imaging and tomography reconstruction. In the latter case, both the spatial and spectral variation may be used to calculate the aforementioned sensitivity profiles.

Reconstructed Results

FIG. 9 shows a comparison of tomographical reconstructions between a linear (902) and a non-linear fluorophore (903). The illustration in FIG. 9 is presented as an example of a quadratic fluorophore. (this case chosen to be quadratic)

The ground truth is shown as the Input anomaly (901) in FIG. 9. Two separate, but close anomalies are shown as the irregular dots in the larger circle.

In the reconstruction using a linear fluorophore (902) the two closely situated anomalies can not be distinguished, as is evident from FIG. 9.

However, a reconstruction using a quadratic fluorophore (902) shows a good separation between the two closely situated anomalies. This can clearly be seen in FIG. 9. This comparison illustrates the advantageous effect that the use of non-linear fluorophores provides, namely a higher contrast and resolution, than with linear fluorophores. The enhancement is due to the more narrow sensitivity while using the quadratic source term as seen in equation (1) below. This can be visualized by considering the collected signal for different source positions. Using a quadratic fluorophore, the signal will only be strong if the source position is in the vicinity of the fluorophore itself. Thus the signal can provide more information about the location of the fluorophore than for the case of a linear fluorophore. This may also give the possibility of resolving, for example, two closely situated fluorophores that are not resolvable using a linear fluorophore, as shown in FIG. 9.

Multi-Beam Fluorescence Diffuse Optical Tomography Using Upconverting Nanoparticles Additionally, this disclosure demonstrate a method in Fluorescence diffuse optical tomography to exploit the unique nonlinear power dependence of upconverting nanoparticles to further increase the amount of information in a raster-scanning setup by including excitation with two beams simultaneously. It was found that the increased information led to more accurate reconstructions.

Fluorescence diffuse optical tomography (FDOT) is a relatively new modality which seeks to reconstruct the spatial distribution of the concentration of fluorescent probes inside turbid material. As an imaging tool, it has a good prospect in biomedical studies to image, for example, tumors, proteases, and drug effects. FDOT has numerically very ill-posed issues. In this issue, the quality of the reconstructions for the fluorescent target is directly determined by the amount and quality of fluorescence information obtained from boundary measurements. Instrumental noise and tissue autofluorescence are the main perturbations of the measurements, resulting in poor signal quality, and can cause severe artifacts in the reconstructed results. In order to overcome this, one could, for example, employ low-noise equipment, use background subtraction or spectral unmixing. However, such methods cannot resolve all issues, since they essentially are only utilizing the present information in a better way rather than adding new constraints for the reconstructions, i.e., adding new independent information, which is critical to improve the quality of the reconstructions. In a noncontact CCD-based FDOT system, one preferred way to gain more information is by increasing the number of excitation positions. However, in order to keep the intensity of the excitation beam within reasonable levels, there is a limit on the minimum size of the excitation beam. This implies a practical upper limit to the highest excitation-position density, since distinct, i.e., non-overlapping, excitation positions are desired for reconstructions. It is also possible to employ an anatomical imaging modality such as magnetic-resonance imaging to provide a-priori structural information. However, this is at the cost of significantly increased complexity and reduced flexibility of the system.

In this disclosure, we present an approach to exploit the quadratic power dependence of upconverting nanoparticles to gain additional information by utilizing two beams simultaneously for excitation in FDOT. The effect of the images taken with dual-beam excitation (named type-D images) on the reconstructions of the nanoparticle number density distribution, n, is demonstrated. In addition, comparisons of reconstructed results between the linear Rhodamine 6G and the quadratic upconverting nanoparticles are made.

The excitation and emission fields can be modeled by two coupled diffusion equations [Ref. 1]. For quadratic fluorophores, the fluorescence signal detected at a fixed detector position under excitation of the kith beam;

can be described by the forward model (1);

$$\Gamma_k = \sum_{i=1}^{N} U_f^*(r_d, r_i) n(r_i) [U_e(r_{s_k}, r_i)]^2 \Delta V_i, \tag{1}$$

where N denotes the number of voxels, $r_{s,d,i}$ denotes the coordinates for source, detector, and $\hat{\Gamma}_k$ voxel, respectively, and;

$\Delta V_i$ is the volume of voxel i.

The forward solution of the excitation light is represented by;

$$[U_e(r_{s,k}, r_i)]^2$$

while the adjoint solution to the forward fluorescence problem is represented by;

$$U_f^*(r_d, r_i).$$

When exciting the medium using two beams simultaneously, the detected signal is given by (2);

$$\Gamma_{k\&j} = \sum_{i=1}^{N} U_f^*(r_d, r_i) n(r_i) \left[U_e(r_{s_k}, r_i) + U_e(r_{s_j}, r_i)\right]^2 \Delta V_i \quad (2)$$

$$= \Gamma_k + \Gamma_j + 2\sum_{i=1}^{N} U_f^*(r_d, r_i) n(r_i) U_e(r_{s_k}, r_i) U_e(r_{s_j}, r_i) \Delta V_i,$$

which reveals the involvement of cross-terms. In a raster-scanning setup (500, 507), if two images are taken sequentially with one excitation beam scanning over two positions (named type-S images), and a third image is taken with two-beam excitation (type-D) above the previous two positions, the involvement of cross-terms implies that the type-D image cannot be obtained by any mathematical manipulation from the existing type-S images, indicating that it is independent and contains additional information. However, for linear fluorophores, e.g., Rhodamine 6G, the type-D image is only linear combinations of the existing type-S images, and will not add more constraints for the inverse problem. For nonlinear fluorophores, it is deduced that Eq. (2) can be generalized to include more simultaneous excitation beams.

The significance of the measurements with dual-beam excitation in the reconstructions was confirmed by the singular-value analysis of the weight matrix, W, whose elements are given by (3) [Ref. 1];

$$W_{(s,d),i} = U_f^*(r_d, r_i)[U_e(r_s, r_i)]^{\gamma} \Delta V_i \quad (3)$$

with;

$\hat{\gamma}^{-}=2$ for quadratic fluorophores and;

$\gamma=1$ for linear fluorophores.

Calculations were performed using the NIRFAST package implementing the finite element method. W was factorized according to (4);

$$W = U \Sigma V^* \quad (4)$$

where U and V are unitary matrices containing the left and right singular vectors of W, and;

$\Sigma$ is a diagonal matrix containing the singular values of W. The column-space of V is spanned by the image-space modes, while the column-space of U is spanned by the detection-space modes. The singular values of W denote how effectively a given image-space mode can be detected by an experimental setup [Ref. 2].

Figure 12:
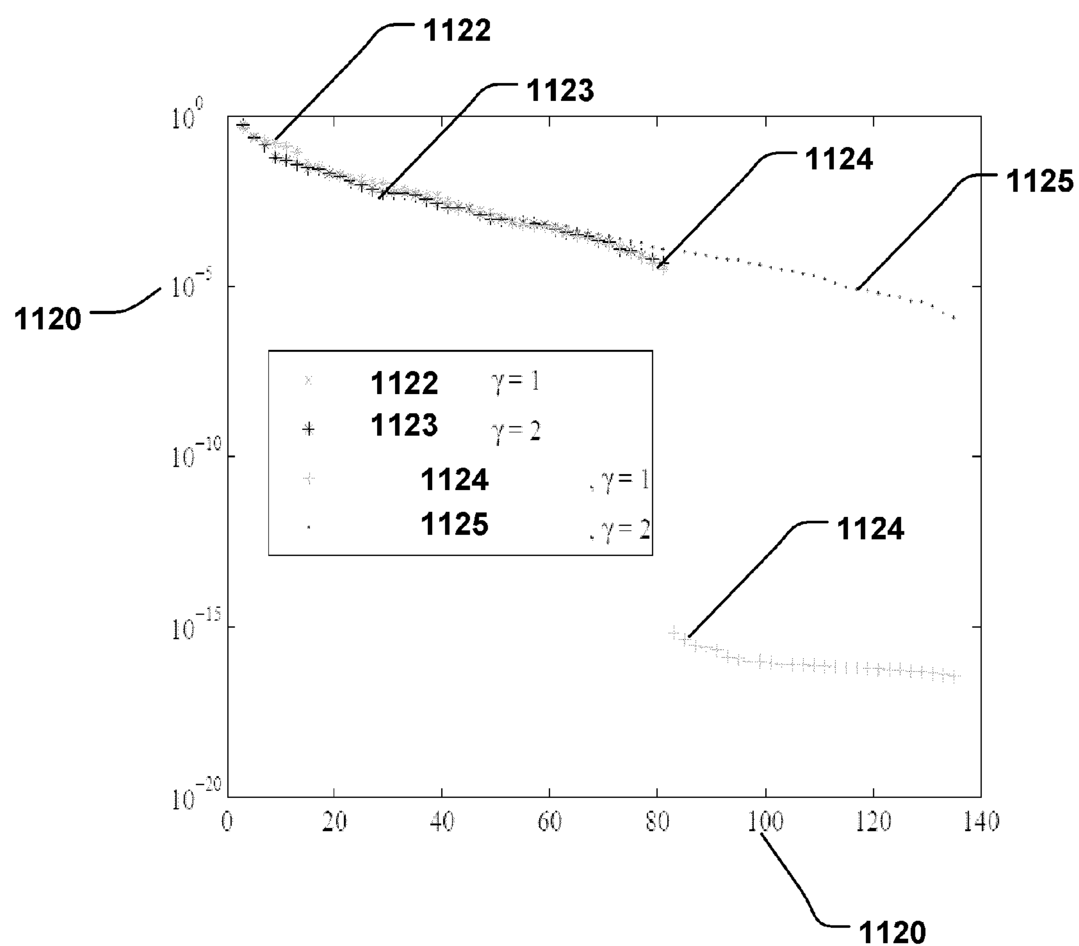
FIG. 12 is a graph showing the normalized singular-value distribution of a weight matrix W, for single-beam excitation and combined single-beam excitation and dual-beam excitation.

FIG. 12 shows the normalized singular-value distribution of W. The x-axis shows the singular value index (1120) and the y-axis shows the normalized singular value intensity (1121). For clarity, only every second singular value are shown. The cross (1122) and plus (1124) signs represent the linear fluorophore ($\gamma=1$), the former for the single-beam excitation (1122), while the latter for the combined single-beam excitation and dual-beam excitation (1124). As seen, the normalized intensities of the additional sigular values due to dual-beam excitation (1124) have dropped to machine precision, which indicates that the measurements with dual-beam excitation may not alleviate the ill-posedness of FDOT. In other words, the type-D images may not provide more information than the existing type-S images. Hence, it may not improve the quality of the reconstructions. However, for the quadratic fluorophore (denoted by asterisk (1123) and dot (1125) signs in FIG. 12, the intensities of the additional singular values (1125) are still significant. This implies that type-D images will contribute to the quality of the reconstructions.

The experiments were carried out in a gelatin phantom with optical properties of $\mu_a=0.29\ cm^{-1}$ and $\mu'_s=10.0\ cm^{-1}$ at 660 nm, measured with a time-of-flight spectroscopy system [Ref. 3]. Two capillary tubes, filled with solutions of Rhodamine 6G (c=0.1 μM) and $NaYF_4$: $Yb^{3+}/Tm^{3+}$ nanoparticles (c=0.1 wt %), respectively, were used to simulate the fluorescent lesions. The experimental setup and corresponding running parameters were similar with those used in our previous work [Ref. 1]. Due to the limited area of the phantom under investigation, only 9 excitation positions (3×3 grid) were used in the present disclosure. The separation of two nearest-neighboring positions was 3.5 mm, and each excitation beam had a diameter of approximately 2.6 mm. During the experiments, a single excitation beam was first used to scan over the 3×3 grid, and one image was captured for each scanned position by a CCD camera. In the next step, two excitation beams, located at two nearest-neighboring sites of the same grid, were simultaneously employed to illuminate the phantom, giving 6 extra type-D images.

Figures 13A, 13B:
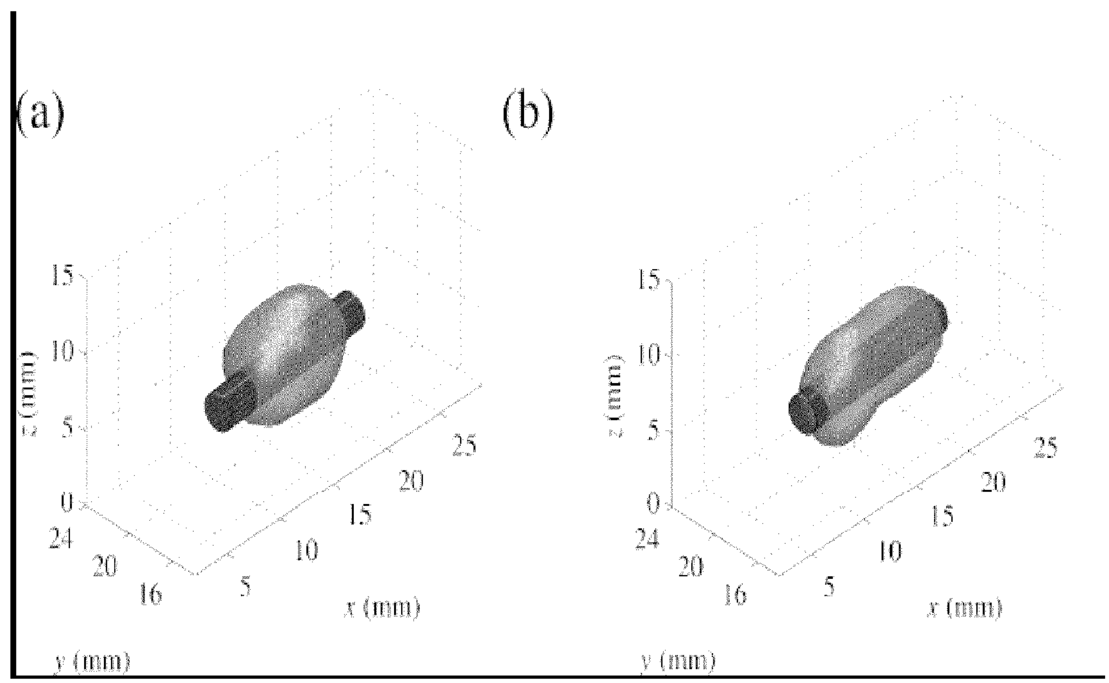
FIGS. 13A and 13B are three-dimensional reconstructions of upconverting nanoparticles, using (10A) only single-beam images, and using (10B) both single-beam and dual-beam images.
Figures 14A, 14B, 14C, 14D, 14E, 14F:
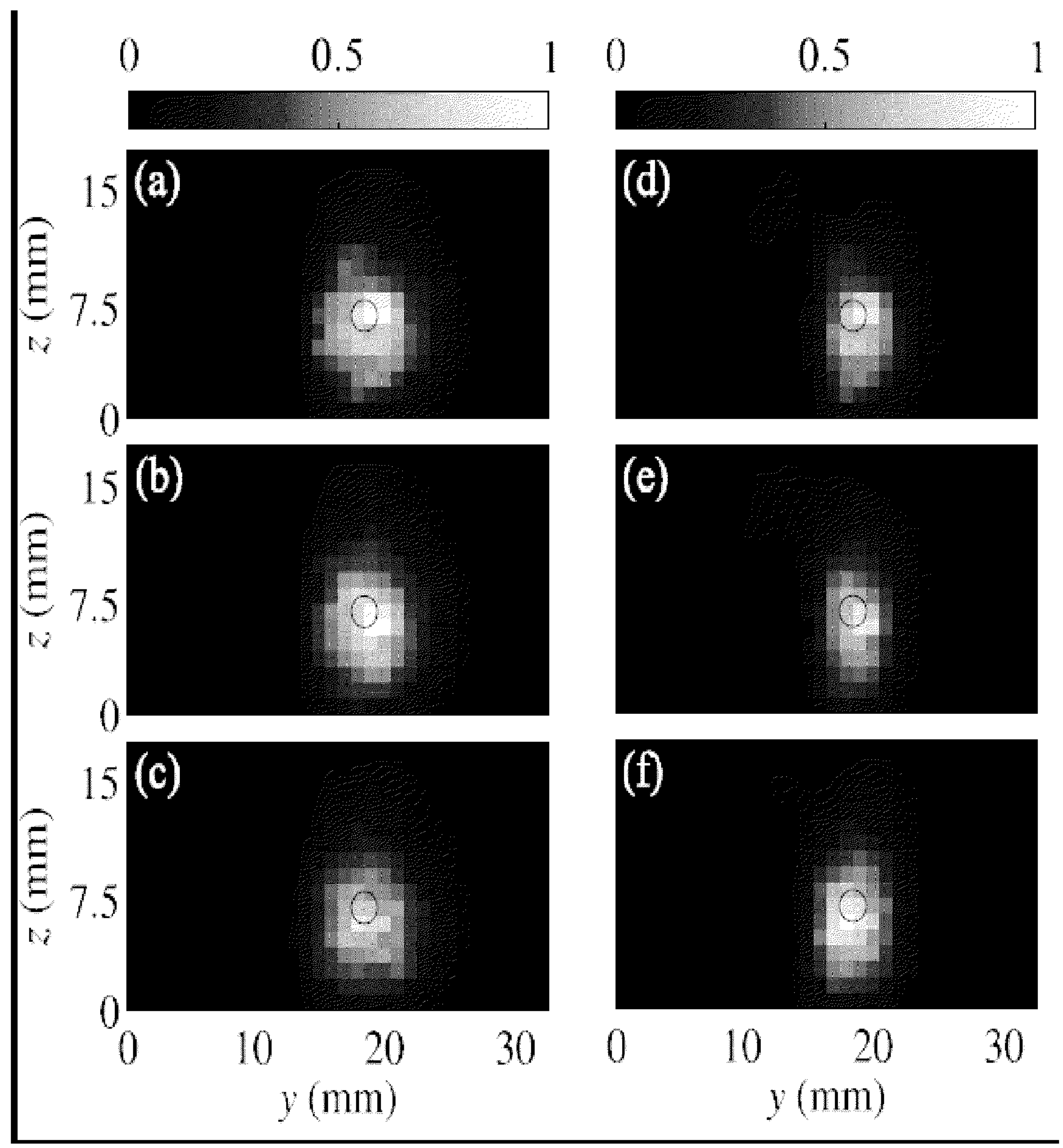
FIGS. 14A to 14F shows cross-sectional slices of the reconstructed relative nanoparticles distribution for reconstructions using (14A-14C) only single-beam images, and using (14D-14F) both single-beam and dual-beam images.
Figures 15A, 15B, 15C, 15D, 15E, 15F:
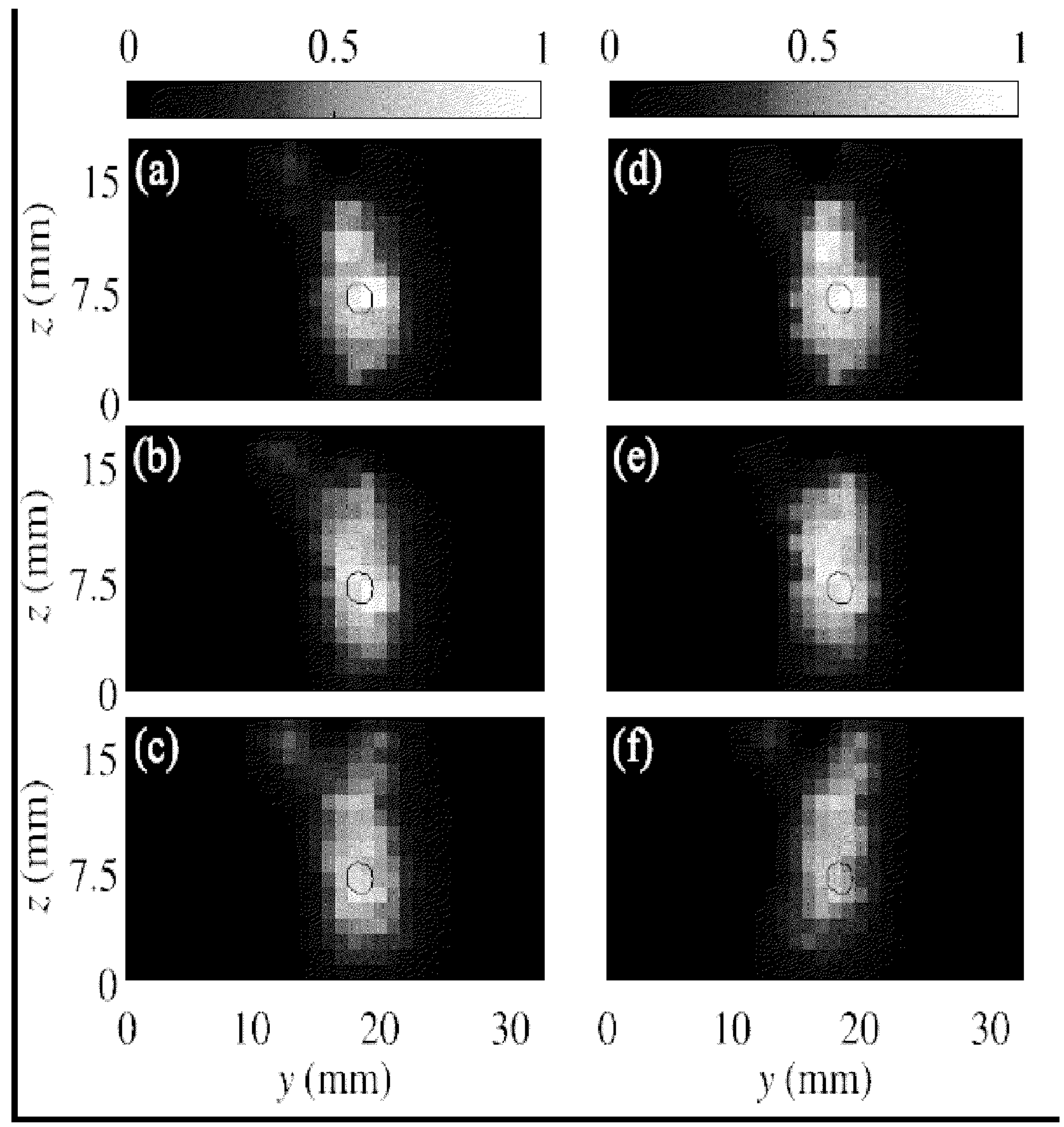
FIGS. 15A to 15F shows cross-sectional slices of the reconstructed relative Rhodamine 6G distribution for reconstructions using (15A-15C) only single-beam images, and using (15D-15F) both single-beam and dual-beam images.

FIGS. 13A-13B shows the three-dimensional rendering of the reconstructed upconverting nanoparticles. The red cylinders in the subfigures are identical and represent the true fluorescent lesions. In the reconstruction of FIG. 13(*a*), only type-S images were used. As can be seen, the shape of the fluorescent lesion is overestimated. This overestimation may be explained by the ill-posedness of the inverse problem. When adding type-D images, the reconstruction of the fluorescent lesion shape is improved remarkably, as shown in FIG. 13B. In order to emphasize the difference between the two reconstructions, cross-sectional slices of the reconstructed relative fluorophore distribution are shown in FIGS. 14A-14F. Although the depth is relatively well reconstructed at the center of the fluorescent lesion (represented by the circles) for both reconstructions, the reconstructed fluorescent lesion is more confined for the case of using both type-S-and-D images. This result confirms that the images of type D indeed contribute to the inverse problem and lead to better reconstructions for the quadratic upconverting nanoparticles. The corresponding reconstructions for the linear Rhodamine 6G were also carried out, whose cross-sectional slices are presented in FIGS. 15A-15F. Compared with the results for the nanoparticles, the reconstructions for Rhodamine 6G do not benefit from adding the type-D images, which is in agreement with the theory. The true depth of the fluorescent lesion is also poorly reconstructed.

It is disclosed an additional unique advantage of the non-linear power dependence of upconverting nanoparticles. This advantage enables the possibility to obtain additional information for the inverse problem by using images taken with two or more excitation beams simultaneously. We found that this resulted in improved reconstructions. The same advantage could not be found when using linear fluorophores, e.g., Rhodamine 6G.

This disclosure presents embodiments of non-linear luminescence imaging and tomography. In experiments it was shown that imaging with upconverting nanocrystals is possible in scattering media resembling biological tissue. Furthermore, simulations showed that it is possible to adapt the theory used in fluorescent optical tomography, to work with the upconverting nanocrystals.

The upconverting nanocrystal particles used in this disclosure, in comparison with organic fluorophores, have a variety of applications, such as for biological markers thanks to their unique optical properties.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

The method may be performed in-vivo at a living human or animal body. In this case, the markers may be preintroduced into the body in any manner, such as by injection into the blood stream or subcutaneously or directly into a tumour, or alternatively by topical application, pulmonary and other non-invasive methods. Such preintroduction can be performed separately from the remaining method. Such preintroduction can be performed in connection with the remaining method but shortly therebefore.

Alternatively or additionally, the method may be performed at a human or animal body, which is sacrifized after the method is performed.

Alternatively or additionally, the method may be performed in vitro at a non-living human or animal body or part of a body, for example a brain-dead human or animal body.

Alternatively or additionally, the method may be performed at non-medical fields, such as filters or tablets.

The following references are incorporated by reference herein in their entirety for all purposes:

[Ref. 1] C. T. Xu, J. Axelsson, and S. Andersson-Engels, Appl. Phys. Lett. 94, 251107 (2009).

[Ref. 2] J. P. Culver, V. Ntziachristos, M. J. Holboke, and A. G. Yodh, Opt. Lett. 26, 701 (2001).

[Ref. 3] E. Alerstam, S. Andersson-Engels, and T. Svensson, J. Biomed. Opt. 13, 041304 (2008).

The invention claimed is:

1. A method of imaging a region in a scattering medium by diffuse luminescence molecular imaging, said region comprising at least one luminescent marker arranged in said scattering medium at a marker position, wherein said luminescent marker is a non-linear luminescent marker, the method comprising:

exciting said luminescent marker by excitation light emitted by one or more light sources into an excitation volume from at least one light source position;

detecting luminescence from said luminescent marker due to said excitation light by a detector at a luminescent light detection position;

providing movement between said light source position and said marker position;

imaging said luminescent marker based on a non-linear dependence of said detected luminescence on said excitation light intensity and said light source position in relation to said marker position, wherein said non-linear dependence is given by the relationship L=k*E^x, wherein:

E is excitation light intensity in said excitation volume;

L is luminescence light intensity from said luminescent marker;

k is a positive constant; and x is a positive number larger than one.

2. The method according to claim 1, wherein providing said movement comprises moving said light source position in relation to said marker position.

3. The method according to claim 2, further comprising scanning said one or more excitation beams between a plurality of said light source positions such that said light source position is moved in relation to said marker position.

4. The method according to claim 3, further comprising:

detecting said luminescence for each of said plurality of light source positions, said luminescence having a total luminescence intensity of said luminescent marker for each of said plurality of light source positions; and imaging said luminescent marker by making an image of said total luminescence intensity for each of said plurality of light source positions.

5. The method according to claim 4, wherein said total luminescence intensity is provided by summing of said luminescence of said luminescent marker.

6. The method according to claim 3, wherein said plurality of light source positions forms a grid pattern, said luminescence marker having a projected area on said grid pattern.

7. The method according to claim 6, wherein said projected area is less than the area covered by said grid pattern.

8. The method according to claim 7, wherein said excitation volume is substantially localized to each of said plurality of light source positions such that said luminescent marker is partially excited if said light source position overlaps partially with said projected area.

9. The method according to claim 6, wherein said one or more light sources are scanned between said plurality of light source positions such that said excitation volume does substantially not overlap between two successive light source positions in said grid pattern.

10. The method according to claim 1, wherein providing said movement comprises moving said marker position in relation to said light source position.

11. The method according to claim 1, comprising exciting said luminescent marker by two or more light sources simultaneously.

12. The method according to claim 1, comprising exciting said luminescent marker by a first light source having a first wavelength from a first light source position, and exciting said luminescent marker by a second light source having a second wavelength from a second light source position.

13. The method according to claim 12, wherein said first wavelength is substantially identical to said second wavelength.

14. The method according to claim 12, wherein said luminescent marker is excited by said first and second light sources simultaneously.

15. The method according to claim 12, wherein at least one of said first and second light source positions is moved in relation to said marker position.

16. The method of claim 1, wherein said diffuse luminescent imaging comprises diffuse luminescent tomography.

17. The method according to claim 16, further comprising;

scanning said one or more light sources between a plurality of different light source positions such that said light source position is moved in relation to said marker position;

detecting said luminescence for providing luminescence images of said luminescent marker for each of said plurality of different light source position; and reconstructing a three-dimensional tomographic image of said luminescent marker from said luminescence images.

18. The method according to claim 17, wherein reconstructing said three-dimensional tomographic image comprises:

calculating an excitation field from said excitation light;

calculating an emission field from said luminescent marker; and calculating a product of said excitation field according to said non-linear dependence, wherein said calculation of said emission field is based on said product.

19. The method according to claim 18, wherein calculating said product comprises multiplying the field strength of said excitation field so as to form a product of said field strength raised to the power corresponding to the power dependence of said non-linear relationship.

20. The method according to claim 19, further comprising calculating the quadratic product of said field strength.

21. The method according to claim 1, wherein providing said movement comprises moving said luminescent light detection position in relation to said marker position.

22. A system for diffuse luminescence molecular imaging of a region of interest in a scattering medium, said system comprising a luminescent marker for use in said luminescent molecular imaging of said scattering medium, wherein said luminescent marker is a non-linear luminescent marker arranged in said scattering medium, said system comprising:

one or more light sources positioned by at least one light source position for exciting said luminescent marker by excitation light emitted by said one or more light sources into an excitation volume; and a detector at a luminescent light detection position detecting luminescence from said luminescent marker due to said excitation light, wherein said luminescent molecular imaging comprises imaging said luminescent marker based on a non-linear dependence of said detected luminescence on said excitation light intensity and said light source position in relation to said marker position, wherein said non-linear dependence is given by the relationship L=k*E^x, wherein:

E is excitation light intensity in said excitation volume;

L is luminescence light intensity from said luminescent marker;

k is a positive constant; and x is a positive number larger than one.

23. The system of claim 22, wherein said luminescent marker is comprised in a group of non-linear luminescent markers configured to upconvert incoming light of an illumination wavelength, such that luminescence occurs at a luminescence wavelength that is shorter than said illumination wavelength when said luminescent marker is illuminated with said incoming light.

24. The system of claim 22, wherein said luminescent marker is a luminescent biological marker, said scattering medium is tissue of a human or animal, and said luminescent biological marker is arranged in said tissue.

25. The system of claim 22, wherein said luminescent marker comprises nanosized upconverting particles.

26. The system of claim 25, wherein said nanosized upconverting particles are of sodium yttrium tetrafluoride ($NaYF4$), co-doped with either $Yb3+/Er3+$ or $Yb3+/Tm3+$.

27. The system of claim 22, wherein said non-linear luminescent marker comprises particles that are water soluble.

28. The system of claim 27, wherein said particles are nanosized upconverting particles that are coated with a structure that is polar.

29. The system of claim 27, wherein said particles are nanosized upconverting particles having hydroxyl groups attached the surfaces of the upconverting particles.

30. The system of claim 22, wherein said marker has a protective coating.

31. The system of claim 22, wherein said luminescent marker is a biological marker that is biofunctionalized.

32. The system of claim 22, wherein said system is devised for luminescence molecular tomography.

33. The system of claim 22, wherein said non-linear markers are attached to an imaging contrast agent for an imaging modality different from a modality for said luminescent imaging.

34. The system of claim 33, wherein said non-linear marker is attached to an organic gadolinium complex or gadolinium compound, which has paramagnetic properties, and wherein said system further comprises a magnetic resonance imaging (MRI) apparatus for simultaneous imaging of said region of interest by MRI and luminescence molecular tomography.

35. The system of claim 22, wherein said incoming light of an illumination wavelength is comprised of two or more excitation beams simultaneously.

36. The system according claim 22, wherein said excitation light is provided by a first light source having a first wavelength from a first light source position, and a second light source having a second wavelength from a second light source position.

37. The system according to claim 36, wherein said excitation light is provided by said first and second light sources simultaneously.

* * * * *